United States Patent
Ha et al.

(10) Patent No.: US 10,155,948 B2
(45) Date of Patent: Dec. 18, 2018

(54) PHARMACEUTICAL COMPOSITION FOR PREVENTING OR TREATING DIABETIC COMPLICATIONS AND SCREENING METHOD FOR PREVENTIVE OR THERAPEUTIC AGENT FOR DIABETIC COMPLICATIONS

(71) Applicants: KANGWON NATIONAL UNIVERSITY UNIVERSITY-INDUSTRY COOPERATION FOUNDATOIN, Gangwon-do (KR);
AMOLIFESCIENCE CO., LTD., Seoul (KR)

(72) Inventors: Kwon-Soo Ha, Gangwon-do (KR); Yeon-Ju Lee, Gangwon-do (KR)

(73) Assignees: Kangwon National University University-Industry Cooperation Foundation and, Gangwon (KR); Amolifescience Co., Ltd., Seoul (KR)

( * ) Notice: Subject to any disclaimer, the term of this patent is extended or adjusted under 35 U.S.C. 154(b) by 0 days.

(21) Appl. No.: 15/593,767

(22) Filed: May 12, 2017

(65) Prior Publication Data
US 2018/0002700 A1    Jan. 4, 2018

(30) Foreign Application Priority Data

May 12, 2016 (KR) .................. 10-2016-0058382
Nov. 22, 2016 (KR) .................. 10-2016-0155641

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 38/17* | (2006.01) |
| *A61K 31/135* | (2006.01) |
| *A61K 31/145* | (2006.01) |
| *A61K 9/00* | (2006.01) |
| *G01N 33/50* | (2006.01) |

(52) U.S. Cl.
CPC ........ *C12N 15/1137* (2013.01); *A61K 9/0019* (2013.01); *A61K 9/0048* (2013.01); *A61K 31/135* (2013.01); *A61K 31/145* (2013.01); *A61K 38/1709* (2013.01); *G01N 33/5023* (2013.01); *C12N 2310/14* (2013.01); *C12N 2320/35* (2013.01)

(58) Field of Classification Search
CPC . A61K 31/713; C12N 2310/11; C12N 15/113
See application file for complete search history.

(56) References Cited

U.S. PATENT DOCUMENTS

2008/0287386 A1    11/2008  Mor et al.
2017/0165207 A1*   6/2017   Eddy et al. .......... A61K 31/713

FOREIGN PATENT DOCUMENTS

| KR | 10-2007-0004569 A | 1/2007 |
| KR | 10-2015-0035713 A | 8/2016 |
| WO | 2012/153125 A1 | 11/2012 |
| WO | 2015/095257 A2 | 6/2015 |

OTHER PUBLICATIONS

Roy et al. (Experimental Eye Research, 142, 2016, 71-75).*
Moe H. Aung et al., "Dopamine Deficiency Contributes to Early Visual Dysfunction in a Rodent Model of Type 1 Diabetes," The Journal of Neuroscience, vol. 34, No. 3, Jan. 15, 2014, pp. 726-736.
Mahendra Prasad Bhatt et al., "C-Peptide Prevents Hyperglycemia-Induced Endothelial Apoptosis Through Inhibition of Reactive Oxygen Species-Mediated Transglutaminase 2 Activation," Diabetes, vol. 62, Jan. 2013, pp. 243-253.
Mahendra P. Bhatt et al.; "C-peptide Replacement Therapy as an Emerging Strategy for Preventing Diabetic Vasculopathy"; Cardiovascular Research; vol. 104; 2014; pp. 234-244.

* cited by examiner

*Primary Examiner* — Amy H Bowman
(74) *Attorney, Agent, or Firm* — Baker & Hostetler LLP

(57) ABSTRACT

Disclosed are a pharmaceutical composition and a method for preventing or treating diabetic complications caused by vascular leakage, comprising a TGase2 inhibitor, and a method of screening a preventive or therapeutic agent for diabetic complications caused by vascular leakage.

8 Claims, 26 Drawing Sheets

Specification includes a Sequence Listing.

FIB. 2C

PHARMACEUTICAL COMPOSITION FOR PREVENTING OR TREATING DIABETIC COMPLICATIONS AND SCREENING METHOD FOR PREVENTIVE OR THERAPEUTIC AGENT FOR DIABETIC COMPLICATIONS

CROSS REFERENCES TO RELATED APPLICATION

This application claims the benefit of Korean Patent Application Nos. KR 10-2016-0058382, filed May 12, 2016, and KR 10-2016-0155641, filed Nov. 22, 2016, which are hereby incorporated by reference in their entireties into this application.

BACKGROUND OF THE INVENTION

1. Technical Field

The present invention relates to a pharmaceutical composition and a method for preventing or treating diabetic complications caused by vascular leakage and a method of screening a preventive or therapeutic agent for diabetic complications.

2. Description of the Related Art

Hyperglycemia and subsequent metabolic changes tend to develop into diabetic complications due to progressive damage and dysfunction of blood vessels. In particular, diabetic retinopathy is one of the most common microvascular complications caused by vascular leakage and is a leading cause of blindness among adults. Diabetic retinopathy is classified into two main types: non-proliferative and proliferative. Non-proliferative diabetic retinopathy is the early stage of the disease, in which chronically high blood sugar from diabetes causes damage to the blood vessels in the retina, resulting in abnormalities in blood flow, loss of retinal pericytes, microaneurysms, basement membrane thickening and vascular leakage. Proliferative diabetic retinopathy is the more advanced form of the disease. During this later stage, many blood vessels in the retina close off, leading to inadequate supply of oxygen (hypoxia). The lack of oxygen in the retina causes new blood vessels to grow. This is called neovascularization and can cause the retina to detach leading to severe vision loss. Thus, in order to prevent the progression of diabetic retinopathy, it is necessary to prevent vasculature alterations and vascular leakage in the retina at an early stage.

Retinal vascular leakage at the early stage of diabetic retinopathy is mainly caused by vascular endothelial growth factor (VEGF)-mediated stress fiber formation and vascular endothelial (VE)-cadherin disruption. Almost all patients with type 1 diabetes and over 60% of patients with type 2 diabetes develop retinopathy. Upregulation of VEGF and its receptors, caused by hyperglycemic conditions, increases intracellular levels of reactive oxygen species (ROS). The increased intracellular ROS generation is directly or indirectly attributed to the loss of stability and internalization of VE-cadherin through microfilament reorganization. However, the precise molecular mechanism by which VEGF induces the disruption of vascular integrity remains unclear.

In addition, transglutaminase 2 (TGase2), also known as tissue transglutaminase, is a member of the transglutaminase family, which catalyzes the cross-linking of proteins via transamidation of glutamine residues to lysine residues in a $Ca^{2+}$-dependent manner. TGase2 is a ubiquitously expressed enzyme that is involved in various cellular processes such as cell death and proliferation, cell adhesion and migration, and cytoskeletal reorganization. TGase2 is also associated with a variety of diseases including cardiovascular diseases, inflammation, celiac disease, neurodegenerative disorders, and hemorrhagic or ischemic stroke. TGase2 is found to be expressed in ocular tissues including the retina and lens and may play a role in ocular diseases including cataracts and glaucoma. However, the role of TGase2 in vascular leakage involved in the pathogenesis of microvascular diabetic complications including retinopathy is not clearly understood.

In this regard, the present inventors revealed that TGase2 plays a critical role in vascular leakage involved in the pathogenesis of microvascular diabetic complications including retinopathy, leading to the present invention.

CITATION LIST

Non-Patent Literature (Non-Patent Document 1) Bhatt M P, Lim Y C, Ha K S. C-peptide replacement therapy as an emerging strategy for preventing diabetic vasculopathy. Cardiovasc Res 2014, 104:234-244

SUMMARY OF THE INVENTION

Accordingly, the present invention has been made keeping in mind the above problems encountered in the prior art, and the present inventors revealed the role of TGase2 in vascular leakage involved in the pathogenesis of microvascular diabetic complications including retinopathy. Therefore, the present invention is intended to provide a pharmaceutical composition and a method for preventing or treating diabetic complications caused by vascular leakage and a method of screening a preventive or therapeutic agent for diabetic complications caused by vascular leakage.

Therefore, the present invention provides a method for preventing or treating diabetic complications caused by vascular leakage comprising: an administering to a subject a pharmaceutical composition comprising a TGase 2 inhibitor and a pharmaceutical composition for preventing or treating diabetic complications caused by vascular leakage, comprising an inhibitor against transglutaminase 2 (TGase2).

In addition, the present invention provides a method of screening a preventive or therapeutic agent for diabetic complications caused by vascular leakage, comprising measuring inhibition of the activity of transglutaminase 2 (TGase2).

It was revealed in the present invention that TGase2 plays a key role in diabetic complications caused by vascular leakage, such as pathological vascular permeability, as well as in diabetic vasculopathy. Employing the pharmaceutical composition for preventing or treating diabetic complications caused by vascular leakage and the screening method for a preventive or therapeutic agent for diabetic complications caused by vascular leakage, TGase2 may be a potent therapeutic target for the treatment of diabetic complications and ocular diseases.

BRIEF DESCRIPTION OF THE DRAWINGS

FIGS. 2A-2D show that TGase inhibitors prevent VEGF-induced stress fiber formation, VE-cadherin disruption and endothelial cell monolayer permeability;

DESCRIPTION OF THE SPECIFIC EMBODIMENTS

Figure 1A:
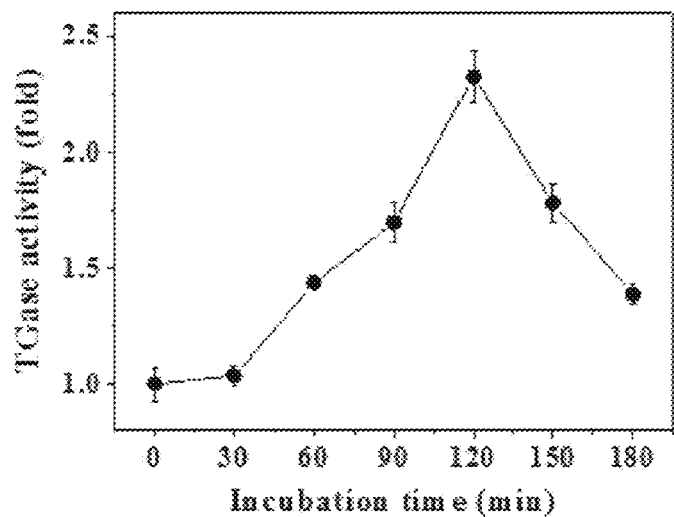
FIGS. 1A-1F show that VEGF-induced TGase2 activation is mediated by elevation of intracellular $Ca^{2+}$ and ROS levels in HRECs.
Figure 1B:
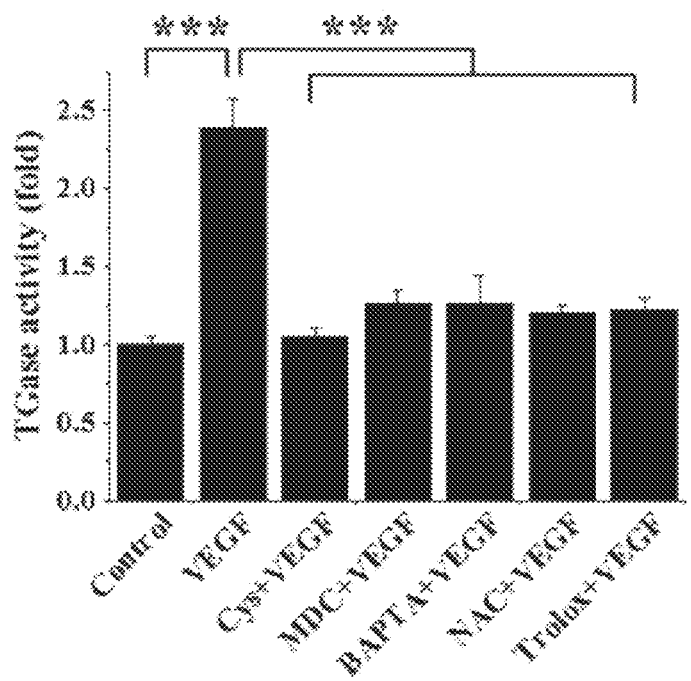

In the present invention, elucidated was the molecular mechanism by which vascular endothelial growth factor (VEGF) induces adherens junction disruption and vascular leakage in the retina of diabetic mice. In detail, the present inventors hypothesized that ROS-mediated TGase activation plays an essential role in VEGF-induced vascular leakage in the diabetic retina, and designed an in-vivo TGase activity assay for mouse retinas, and demonstrated that hyperglycemia activates TGase2 in the diabetic retina to induce vascular leakage. A TGase inhibitor or TGase2 siRNA prevented VEGF-induced stress fiber formation and VE-cadherin disruption in human retinal endothelial cells (HRECs). The in-vitro results were validated in vivo using streptozotocin-induced diabetic mice. The present inventors found that in-vivo TGase activity was increased in the diabetic retina and that intravitreal injection of TGase inhibitor and TGase2 siRNA prevented hyperglycemia-induced TGase activation and vascular leakage in the diabetic retina. The role of TGase2 in VEGF-induced vascular leakage was further demonstrated in diabetic TGase2$^{-/-}$ mice. These findings indicate that TGase2 plays a pivotal role in VEGF-induced vascular integrity disruption and vascular leakage in the diabetic retina.

Hereinafter, the present invention will be described in detail with regard to the following features.

The present invention relates to a method and a pharmaceutical composition for preventing or treating diabetic complications caused by vascular leakage comprising a transglutaminase 2 (TGase2) inhibitor, and a method of screening a preventive or therapeutic agent for diabetic complications caused by vascular leakage.

The present inventors found that vascular endothelial growth factor (VEGF) activates TGase2 through the sequential elevation of intracellular $Ca^{2+}$ and ROS levels and induces the breakdown of vascular integrity through stress fiber formation and VE-cadherin disruption. ROS-mediated TGase2 activation played a critical role in the VEGF-induced breakdown of vascular integrity in endothelial cells and hyperglycemia-induced microvascular leakage in the retina of diabetic mice. Thus, TGase2 may be a potential therapeutic target for treating diabetic complications caused by vascular leakage or ocular diseases associated with TGase2. Also, a pharmaceutical composition comprising an inhibitor against TGase2 may be useful in preventing and treating diabetic complications caused by vascular leakage.

The diabetic complications in the present invention may be caused by the disruption of vascular integrity, which is induced by vascular endothelial growth factor (VEGF). In detail, the diabetic complications may be any one selected from among diabetic retinopathy, diabetic cardiovascular diseases, diabetic stroke, diabetic nephropathy, diabetic peripheral neuropathy and diabetic cancer metastasis, and diabetic retinopathy may be preferable. The diabetic complication caused by vascular leakage may be induced by hyperglycemia.

The transglutaminase 2 (TGase2) inhibitor according to the present invention includes all of substances inhibiting TGase2 activity, and may be a TGase2-specific siRNA or C-peptide. TGase2 inhibitors can be divided into three classes depending on their inhibitory mechanism to TGase2: competitive inhibitors, reversible inhibitors and irreversible inhibitors. The TGase2 inhibitor according to the present invention includes all inhibitors of these three classes. The competitive inhibitor may be one or more selected from among putrescine, 5-(biotinamido)pentylamine, monodansylcadaverine (MDC), cystamine, dopamine, cysteamine, 2-mercaptoethylamine (MEA), ethanolamine, spermidine, histamine and fluorescein cadaverine. The reversible inhibitor may be one or more selected from among GTP, GMP- PCP, GTPγS, GDP, LDN-27219, GK13 [2-(phenylethynyl)-3-(2-(pyrrolidin-1-yl)ethoxy)quinoxaline] and GK921 [2-(phenylethynyl)-3-(2-(pyridin-2-yl)ethoxy)pyrido[3,2-b]pyrazine]], and the irreversible inhibitor may be any one selected from among iodoacetamide, 3-halo-4,5-dihydroisoxazles, carbobenzyloxy-L-glutaminylglycine (Cbz-gln-gly), β-unsaturated amides, epoxides, 1,2,4-thiadiazoles, maleinimides, chloroacetamides, gluten peptide sequence, factor XIIIa inhibitor and 2-[(2-oxopropyl)thio imidazolium] derivates. However, the inhibitors are not limited thereto.

In particular, the TGase2 inhibitor is preferably one or more selected from among monodansylcadaverine (MDC), cystamine, cysteamine, dopamine, ethanolamine, a C-peptide and a TGase2-specific siRNA.

Several low-molecular-weight inhibitors have been known to inhibit the transamidation activity of TGase2, and cystamine is the most commonly used in vivo to inhibit TGase activity, preferably TGase2 activity. Cystamine is used for the treatment of corneal crystals in nephropathic cystinosis. Also, cystamine was used in clinical trials for Huntington's disease and cystic fibrosis. In the present invention, it was revealed that cystamine and monodansylcadaverine (MDC) inhibit VEGF-induced ROS generation and TGase2 activation and thus prevent vascular leakage in the retina.

In addition, dopamine, which functions as a neurotransmitter, protects nerve cells in the brain and inhibits TGase activity, preferably TGase2 activity. According to the present invention, it was found that dopamine inhibits VEGF-induced ROS generation and TGase activation and thus prevents vascular leakage.

Figure 11:
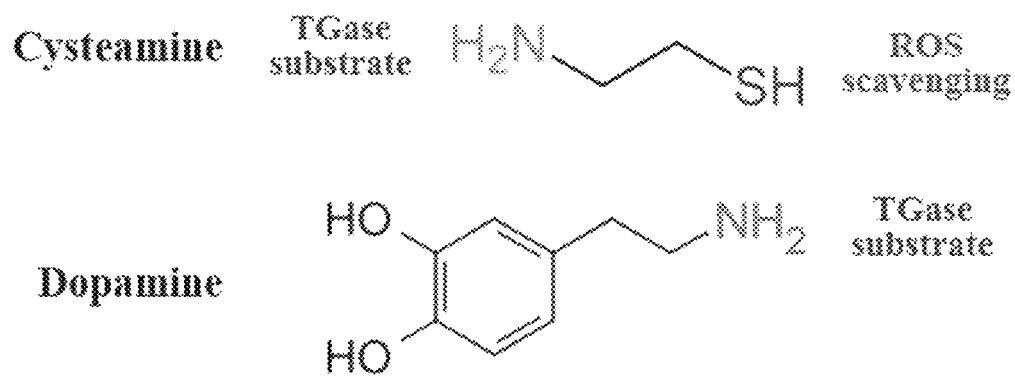
FIG. 11 shows the chemical structure of cysteamine and dopamine.

As seen in FIG. 11, cysteamine is a monomer or reduced form of cystamine, and it has antioxidant activity as well as an inhibitory effect to TGase activity, preferably TGase2 activity. In the present invention, it was found that cysteamine inhibits VEGF-induced ROS generation and TGase activation and thus prevents vascular leakage.

In this regard, the present inventors conducted research to assess in-vivo TGase activity and vascular leakage in the early stage of diabetic retinopathy, and the research resulted in the finding that TGase2 is a critical enzyme. Also, it was found that cystamine, monodansylcadaverine, dopamine and cysteamine inhibit VEGF-induced ROS generation and TGase2 activation in the retina and thus prevent vascular leakage.

The siRNA may have a sequence of 5'-AAGAGCGAGAUGAUCUGGAAC-3' (SEQ ID NO. 1). The TGase2-specific siRNA of the present invention may be another target molecule that is able to be topically applied to the eye so as to prevent diabetic complications caused by vascular leakage or other ocular diseases associated with TGase2.

Figure 5A:
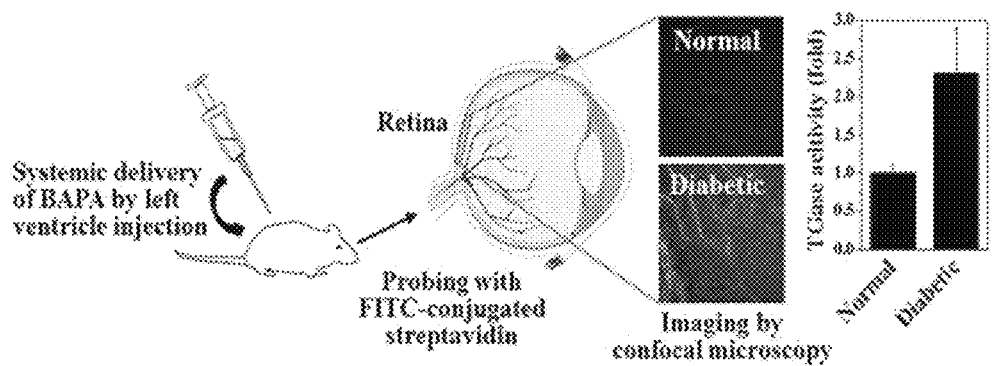
FIGS. 5A-5C show that the in vivo TGase activity is elevated in the retinas of diabetic mice or is inhibited by intravitreal injection of C-peptide and various inhibitors.

The C-peptide may have a sequence of EAEDLQVGQVELGGGPGAGSLQPLALEGSLQ (SEQ ID NO. 2). In particular, the C-peptide may be a human C-peptide, which is a 31-amino acid peptide that is co-secreted with insulin in equimolar concentrations by pancreatic β cells into the peripheral circulatory system. C-peptide prevents diabetic vasculopathy by inhibiting ROS-mediated TGase2 activation and endothelial apoptosis. Also, C-peptide prevents VEGF-mediated microvascular permeability by inhibiting ROS-mediated stress fiber formation and VE-cadherin disruption in the retina of diabetic mice. In the present invention, it was found that, when intravitreally administered, C-peptide prevents ROS-mediated TGase2 activation in the diabetic retina. Thus, C-peptide may exert a beneficial effect on diabetic vasculopathy and retinopathy by inhibiting intracellular events involving ROS and TGase2 (FIG. 5C).

The TGase2 inhibitor may inhibit VEGF-induced TGase2 activation, and may prevent the VEGF-induced breakdown of vascular integrity and retinal microvascular leakage, which are caused by TGase2 activation.

The TGase2 inhibitor may have an antioxidant effect.

In endothelial cells, the adherens junctions are composed of VE-cadherin and several protein partners including β-catenin. VE-cadherin directly interacts with β-catenin, and VEGF induces adherens junction disruption through their tyrosine phosphorylation and subsequent dissociation. In ovarian cancer cells, TGase2 recruits c-Src, which in turn phosphorylates β-catenin and releases β-catenin from E-cadherin. Thus, the present inventors examined whether β-catenin and c-Src can participate in VEGF-induced adherens junction disruption and vascular leakage. In the present invention, the TGase2 inhibitor cystamine inhibited VEGF-induced c-Src phosphorylation, β-catenin breakdown and endothelial permeability in human retinal endothelial cells (HRECs). Dasatinib, which blocked VEGF-induced c-Src phosphorylation, also prevented VEGF-induced β-catenin breakdown and endothelial permeability. These findings indicate VEGF induces vascular leakage in endothelial cells through TGase2-mediated intracellular events involving c-Src phosphorylation, dissociation of β-catenin from VE-cadherin and subsequent adherens junction breakdown.

Meanwhile, the composition of the present invention is a pharmaceutical composition, which may further comprise a pharmaceutically acceptable carrier, excipient or diluent. The term "pharmaceutically acceptable carrier, excipient or diluent", as used herein, is intended to include any and all solvents, dispersion media, coatings, adjuvants, stabilizers, diluting agents, preservatives, antibacterial and antifungal agents, isotonic and absorption delaying agents, and the like. Examples of carriers, excipients and diluents, which can be contained in the pharmaceutical composition, include lactose, dextrose, sucrose, sorbitol, mannitol, xylitol, maltitol, starches, glycerin, acacia rubber, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate, mineral oil, and the like.

The present composition may be formulated into oral dosage forms, such as powders, granules, tablets, capsules, suspensions, emulsions, syrups and aerosols, and sterile injectable solutions according to the methods commonly known in the art. The pharmaceutical preparations may be prepared using commonly used diluents or excipients, such as fillers, thickening agents, binders, wetting agents, disintegrators, surfactants, and the like. Solid preparations for oral administration may include tablets, pills, powders, granules, and capsules. For these solid preparations, the present composition may be mixed with at least one or more excipients, for example, starch, calcium carbonate, sucrose or lactose, and gelatin.

In addition to simple excipients, lubricants such as magnesium stearate or talc may be also employed. Liquid preparations for oral administration include suspensions, solutions, emulsions, syrups, and the like. These preparations may include commonly used simple diluents, such as water and liquid paraffin, and if desired, may further include various excipients, for example, wetting agents, sweeteners, aromatics and preservatives. Preparations for parental administration include sterile aqueous solutions, non-aqueous solutions, suspensions, emulsions, freeze-dried preparations, and the like. Non-aqueous solutions and suspensions may be prepared using propylene glycol, polyethylene glycol, vegetable oils such as olive oil, and injectable esters such as ethyloleate.

The present composition may be administered via any of the common routes if it is able to reach to a desired tissue. Preferable is subcutaneous injection, intradermal injection, intravenous injection, intraperitoneal injection or intravitreal injection using an osmotic pump.

The composition or TGase2 inhibitor of the present invention may be administered in an effective amount or a pharmaceutically effective amount. The term "effective amount" or "pharmaceutically effective amount", as used herein, refers to an amount sufficient to provide a preventive or therapeutic effect but not so much as to cause any side effects or severe or excess immune responses. An effective dosage of the present composition may vary depending on various factors including the type of disease, severity of the illness, drug activity, administration route, excretion rate, duration of treatment, drugs used in combination or simultaneously, the patient's age, body weight, gender, dietary habits and general health state, and other factors known in pharmaceutical or medical fields. Various factors that are taken into account in determining the "effective amount" or "pharmaceutically effective amount" are known to those skilled in the art, and for instance, are described in the following references [Gilman et al., eds., Goodman And Gilman's: The Pharmacological Bases of Therapeutics, 8th ed., Pergamon Press, 1990] and [Remington's Pharmaceutical Sciences, 17th ed., Mack Publishing Co., Easton, Pa., 1990].

In particular, for the prevention or treatment of diabetic retinopathy, the present composition may be administered by intravitreal injection at a single dose as follows: C-peptide may be administered at a single dose of from 0.03 µg to 30 µg, cystamine at a single dose of from 0.11 mg to 112.6 mg, monodansylcadaverine at a single dose of from 0.06 mg to 66.5 mg, dopamine at a single dose of from 0.96 µg to 962.5 µg, cysteamine at a single dose of from 0.39 mg to 394 mg, and TGase2 siRNA at a single dose of from 0.66 nmol to 660 nmol. Also, for subcutaneous injection, intravenous injection, intraperitoneal injection, and the like using an osmotic pump, the inhibitors may be administered at a blood concentration of from 0.01 nM to 10 nM for C-peptide, from 0.5 µM to 500 µM for cystamine, from 0.2 µM to 200 µM for monodansylcadaverine, from 0.005 µM to 5 µM for dopamine, from 0.005 mM to 5 mM for cysteamine, or from 1 nM to 1000 nM for TGase2 siRNA. However, the administration dose is not limited to the above ranges, and may vary within the daily dose depending on the patient's weight, age, gender, health state and diet, administration time, administration route, excretion rate, and severity of illness.

Based on the fact that approximate axial eye lengths are 3 mm for mice and 24 mm for humans and the human eye has a 512-fold larger vitreous volume compared to the mouse eye, the administration dose for the human eye is 512 times greater than that for the mouse eye, and thus, the intravitreal dose ranges for the human were calculated as 1/100 to 10 times of the administration dose. The blood concentration ranges of the inhibitors for subcutaneous injection, intravenous injection, intraperitoneal injection, and the like using an osmotic pump were calculated as 1/100 to 10 times of the concentration with which cells are treated.

In addition, the present invention relates to a method of screening a preventive or therapeutic agent for diabetic complications caused by vascular leakage, comprising measuring the inhibition of TGase2 activity. In detail, the method may comprise detecting the inhibition of TGase2 activity. Since TGase2 may be a potential therapeutic target for treating diabetic complications caused by vascular leakage or ocular diseases associated with TGase2, the measurement of the inhibition of TGase2 activity enables screening for a preventive or therapeutic agent for diabetic complications caused by vascular leakage. The inhibition of TGase2 activity may be measured in non-proliferative diabetic retinopathy, which is an early stage of the disease and is a diabetic complication caused by vascular leakage. The inhibition of TGase2 activity and inhibitory capacity against TGase2 may be detected by measuring the fluorescence intensity of FITC-conjugated streptavidin, and TGase2 activity may be thus quantitatively analyzed by confocal microscopy. For example, 5-(biotinamido)pentylamine (BAPA) was injected into the left ventricle to be systemically delivered into the circulatory system, the retina is then probed with FITC-conjugated streptavidin, and TGase2 activity is measured by confocal microscopic imaging, without being limited thereto.

Diabetic complications developing from vascular leakage, such as diabetic retinopathy, are predominantly caused by vascular endothelial growth factor (VEGF)-induced vascular leakage. In detail, it has been known that high glucose induces metabolic abnormalities and thus leads to blood flow alteration in retinal microvascules, loss of retinal pericytes, vascular leakage, and so on, and that VEGF is the major cause of vascular leakage in the diabetic retina. However, the basic mechanism has been unknown. In this regard, the present inventors designed an in-vivo TGase activity assay in mouse retina and demonstrated that hyperglycemia induces vascular leakage by activating TGase2 in the diabetic retina. It was found that VEGF activates TGase2 through sequential elevation of intracellular $Ca^{2+}$ and ROS levels and that TGase inhibitors, cystamine, monodansylcadaverine (MDC), cysteamine, dopamine, C-peptide and ethanolamine, or a TGase2 siRNA prevented VEGF-induced stress fiber formation and VE-cadherin disruption, which play a critical role in modulating endothelial permeability. Intravitreal injection of TGase inhibitors and a TGase2 siRNA successfully prevented hyperglycemia-induced TGase2 activation and microvascular leakage in the retina of diabetic mice. C-peptide or ROS scavengers were also found to inhibit TGase activation in the retina of diabetic mice. The role of TGase2 in VEGF-induced vascular leakage was further confirmed in diabetic TGase2$^{-/-}$ mice. Thus, these findings indicate that ROS-mediated activation of TGase2 plays a key role in VEGF-induced vascular leakage by stimulating stress fiber formation and VE-cadherin disruption.

The present invention will be explained in more detail with reference to the following examples and test examples in conjunction with the accompanying drawings. However, the following examples and test examples are provided only to illustrate the present invention but are not to be construed as the limit of present invention.

REFERENCE EXAMPLES (1) Cell Culture

HUVEC isolation was done by our own supply and Human retinal endothelial cells (HRECs) were purchased from the Applied Cell Biology Research Institute (Cell Systems, Kirkland, Wash.). Both respectively were grown on 2% gelatin-coated plates in a M199 medium supplemented with 20% fetal bovine serum (FBS), 3 ng/ml basic fibroblastic growth factor, 5 units/ml heparin, 100 units/ml penicillin, and 100 µg/ml streptomycin. For experiments, cells were incubated for 6 hrs in a low-serum medium supplemented with 1% FBS and antibiotics.

(2) Measurement of Intracellular $Ca^{2+}$ Levels and ROS Generation

Changes in intracellular $Ca^{2+}$ levels were monitored as previously described. Cells on coverslips were co-incubated with 2 µM Fluo4-AM and various inhibitors for 30 min at 37° C. Coverslips were scanned every 10 sec in the presence of 10 ng/ml VEGF using a confocal microscope (FV-300, Olympus Tokyo, Japan). Single-cell fluorescence intensities of peaks were determined for 10 randomly selected cells per trial.

Intracellular ROS generation was determined using 2',7'-dichlorodihydrofluorescein diacetate ($H_2$DCFDA, Molecular Probes, Eugene, Oreg.) staining as previously described. Cells were pretreated with inhibitors for 30 min and co-incubated with 10 ng/ml of VEGF and 10 µM $H_2$DCFDA in low-serum media (phenol red-free) for 10 min. Labeled cells were immediately analyzed using confocal microscopy (Fluoview-300, Olympus). Single-cell fluorescence intensities were determined for 10 randomly selected cells per test. Intracellular ROS levels were determined by comparing average fluorescence intensities of treated cells with those of control cells (expressed as multiples thereof).

(3) Measurement of In Situ TGase Activity

In-situ Tgase transamidating activity was determined via confocal microscopic assay according to a previously known procedure. In brief, cells were incubated with 1 mM 5-(biotinamido)pentylamine (BAPA) for 1 hr at 37° C., fixed with 3.7% formaldehyde in PBS for 30 min, and permeabilized with 0.2% Triton X-100 in PBS for 30 min. After incubation with a blocking solution of 2% BSA in 20 mM Tris (pH 7.6), 138 mM NaCl, and 0.1% Tween 20 for 30 min, cells were treated with Cy3-conjugated streptavidin (1:200, v/v) in the blocking solution for 1 hr. Single-cell fluorescence intensities of stained cells were determined using confocal microscopy for 10 randomly selected cells per test. TGase activities were determined by comparing average fluorescence intensities of treated cells with those of control cells (expressed as multiples thereof).

(4) Transfection with Human TGase2-Specific Small Interfering RNA (siRNA)

HRECs were transfected with human TGase2-specific siRNA as described previously. In brief, cells were transfected with various concentrations of human TGase2-siRNA or 100 nM control siRNA (Dharmacon, Lafayette, Colo.) using siLentFect lipid reagent (Bio-Rad Laboratories, Hercules, Calif.) according to the manufacturer's instructions. Six hours after transfection with the indicated concentrations, the medium was replaced with a fresh culture medium and the transfected cells were further incubated for 24 hrs.

(5) Western Blot Analysis

Cells were incubated with an ice-cold lysis buffer containing 50 mM Tris-HCl (pH 7.5), 1% Triton X-100, 150 mM NaCl, 1 mM EDTA, 0.1 mM phenylmethylsulfonyl fluoride (PMSF), 10 µg/ml aprotinin, and 10 µg/ml leupeptin for 30 min. Cell lysates were separated by SDS-PAGE and transferred to polyvinylidene fluoride membranes. The membranes were blocked with 5% skim milk in TBS with 0.1% Tween for 1 hr at room temperature (RT). The membranes were probed with an anti-TGase2 antibody (Santa Cruz Biotechnology, Santa Cruz, Calif.) and phospho-Src ($Tyr^{416}$) antibody (Cell Signaling Technology, Danvers, Mass.), followed by incubation with a horseradish peroxidase-conjugated secondary antibody. Protein bands were visualized using a chemiluminescent substrate (Pierce, Rockford, Ill.).

(6) Visualization of Actin Filaments, VE-Cadherin and β-Catenin in HRECs

Actin filaments and VE-cadherin were visualized as previously described. For visualization of actin filaments, cells were treated with 10 ng/ml VEGF for 1 hr at 37° C., fixed with 3.7% formaldehyde, and permeabilized with 0.2% Triton X-100. Cells were incubated with Alexa Fluor 488 phalloidin (1:200, Molecular Probes) for 1 hr at RT and actin filaments were observed with a confocal microscope. For visualization of VE-cadherin, cells were preincubated with the TGase2 inhibitors for 30 min and treated with 10 ng/ml VEGF for 90 min at 37° C. Following fixation and permeabilization, cells were incubated overnight with a monoclonal anti-VE-cadherin antibody (1:200, Santa Cruz Biotechnology) at 4° C. Cells were then probed with an FITC-conjugated goat anti-mouse antibody (1:200, Sigma) and VE-cadherin was visualized using confocal microscopy. Adherens junctions are represented by histograms of VE-cadherin as indicated by dotted lines and were quantitatively analyzed using peak fluorescence intensities of the histograms at the single-cell level for 10 randomly selected cells per experiment.

For visualization of β-catenin, cells were preincubated with inhibitors for 30 min and treated with 10 ng/ml VEGF for 90 min, fixed with 3.7% formaldehyde, and permeabilized with 0.2% Triton X-100. Cells were incubated overnight with a monoclonal anti-3-catenin antibody (1:200, Santa Cruz Biotechnology) at 4° C. Cells were then probed with an FITC-conjugated goat anti-mouse antibody (1:200, Sigma) and visualized using confocal microscopy. Images for making galleries were cropped to a smaller size using Microsoft PowerPoint 2010 software.

(7) In-Vitro Permeability Assay

In-vitro permeability assay was performed as previously described. HRECs were grown on gelatin-coated inserts (0.4 µm polycarbonate membrane) of Transwell® Permeable Supports (Costar, Corning, N.Y., USA) up to confluence. Approximately $1.0×10^5$ cells in 0.5 ml of culture medium were seeded on the upper side of the membrane while 1 ml of culture medium was added to the lower compartment. After culturing for five days, cells on the inserts were pre-incubated with 50 µM cystamine, 20 µM monodansyl-cadaverine (MDC), or 100 nM dasatinib (BioVision, Milpitas, Calif.) for 30 min, treated with 10 ng/ml VEGF for 90 min, and incubated with 1 mg/ml 40 kDa FITC-dextran (Sigma) for the last 60 min. The amount of FITC-dextran that diffused through the endothelial monolayer into the lower chamber was measured using a microplate spectrofluorometer (Molecular Devices, Sunnyvale, Calif., USA).

(8) Intravitreal Injection of Inhibitors or Mouse TGase2 siRNA

Two weeks after streptozotocin injection, diabetic mice were intravitreally injected with 2 µl of TGase inhibitors (50 mM cystamine or 20 mM MDC), 1 µM C-peptide (American Peptide Company, Sunnyvale, Calif.), ROS scavengers (2 µM Trolox or 500 mM NAC), or 65 µM mouse TG2-specific siRNA (Dharmacon, Lafayette, Colo.) into one eye and an equal volume of PBS or mouse control siRNA (Dharmacon, Lafayette, Colo.) into the contralateral eye. Non-diabetic mice were also intravitreally injected with 2 µl of PBS or mouse control siRNA into the eyes. After 24 hrs for inhibitors or C-peptide or 48 hrs for mouse TGase2 siRNA, mice were subjected to measurement of in-vivo TGase activity and vascular leakage from the retina.

(9) Measurement of In-Vivo TGase Activity in Mouse Retina

In vivo Tgase transamidating activity was determined in mouse retina using confocal microscopy (FIG. 5A). 24 hrs after intravitreal injection of TGase2 inhibitors and C-peptide or 48 h after the injection of mouse TGase2-specific siRNA, mice were deeply anaesthetized using 2.5% avertin and 48 µl of 100 mM BAPA was injected into the left ventricle. BAPA was allowed to circulate for 10 min and mice were sacrificed by cervical dislocation. Eyes were then enucleated and immediately fixed with 4% paraformaldehyde for 45 min. Retinas were dissected in the Maltese cross-configuration and permeabilized with 0.2% Triton X-100 in PBS for 30 min at RT. After incubation with the blocking solution for 30 min, retinas were treated with FITC-conjugated streptavidin (1:200, v/v) in the blocking solution for 1 hr at RT. The superficial vessels of stained retinas (n=8 per group) were observed using confocal microscopy and fluorescence intensities were analyzed using Fluoview software (FV-300). In-vivo TGase activities were quantitatively determined using fluorescence intensities in the retinas of normal and diabetic mice.

(10) Measurement of Vascular Leakage in Mouse Retina

Microvascular leakage in mouse retina was investigated via the fluorescein angiography method as previously described. In brief, 24 hrs or 48 hrs after intravitreal injection of TGase2 inhibitors or mouse TGase2 siRNA, respectively, mice were deeply anaesthetized and 1.25 mg of 500 kDa FITC-dextran (Sigma) was injected into the left ventricle. The dye was allowed to circulate for 5 min and mice were sacrificed via cervical dislocation. The eyes were enucleated and immediately fixed with 4% paraformaldehyde for 45 min. Retinas were dissected in the Maltese cross-configuration and flat-mounted onto glass slides. The superficial vessels of the retinas (n=8 per group) were observed by confocal microscopy and vascular leakage was quantitatively analyzed using the Fluoview software by determining the fluorescence intensities of FITC-dextran extravasated from the retina vessel.

(11) Visualization of Actin Filaments and VE-Cadherin in Mouse Retina

For staining actin filaments, mice were sacrificed by cervical dislocation, and eyes were enucleated and immediately fixed overnight with 4% paraformaldehyde at 4° C. Following dissection in the Maltese cross-configuration, retinas were permeabilized with 1.0% Triton X-100 in PBS for 1 hr and incubated with Alexa Fluor 488 phalloidin (1:200, Molecular Probes) for 2 hrs at RT. For staining VE-cadherin, enucleated eyes were fixed with 4% paraformaldehyde at RT for 45 min and acetone for 3 min at −20° C. Following dissecting in the Maltese cross-configuration, retinas were permeabilized with 1.0% Triton X-100 in PBS for 4 hrs at RT and incubated overnight with a monoclonal VE-cadherin antibody (1:100, BD Pharmingen) at 4° C. Retinas were then incubated with an FITC-conjugated goat anti-mouse antibody (1:300, Sigma) for 2 hrs at RT. Actin filaments and VE-cadherin in the superficial vessels of retinas were visualized by confocal microscopy.

(12) Immunohistochemistry and Visualization of TGase Expression

Mouse eyes were fixed overnight with 4% paraformaldehyde at 4° C., incubated overnight with 30% sucrose at 4° C., and frozen in OCT. Frozen sections were cut at 10 µm using a microtome-cryostat (Leica Biosystems, Wetzlar, Germany) and washed three times with PBS. Antigen retrieval was performed with 0.01 M citrate buffer (pH 6.0) for 20 min at 95° C. Following cooling for 20 min at RT, sections were rinsed three times with 0.1% Tween 20 in PBS and incubated with the blocking solution for 30 min. Sections were then incubated overnight with an anti-TGase2 antibody (1:200, Santa Cruz Biotechnology) in the blocking solution and probed with an FITC-conjugated goat anti-rabbit antibody (1:300, Sigma) for 2 hrs at RT. TGase2 expression was visualized via confocal microscopy.

(13) Statistical Analysis

Data processing was performed using Origin 6.1 software (OriginLab, Northampton, Mass.) and expressed as mean±SD of at least three independent trials. Statistical significance was determined using ANOVA. Values of $p<0.05$ were considered statistically significant.

Example 1: Generation of TGase2$^{-/-}$ and Diabetic Mouse Models

Six-week-old male C57BL/6 mice were obtained from KOATECH (Pyeongtaek, Korea). TGase2$^{-/-}$ mice (C57BL/6) were prepared by disrupting exons 5 and 6 of TGase2 by homologous recombination, as previously described. Diabetic mice were generated by a single intraperitoneal injection of streptozotocin (150 mg/kg body weight, Sigma) freshly prepared in 100 mM citrate buffer (pH 4.5) as previously described. Genotyping and clinical data of TGase2$^{-/-}$ mice are given in FIGS. 1A-1F. Mice with non-fasting blood glucose levels greater than 19 mM, polyuria and glucosuria were considered diabetic. Experiments were performed in strict accordance with the guidelines of the Institutional Animal Care and Use Ethics Committee of Kangwon National University.

Test Example 1: Evaluation of Whether VEGF Activates TGase2 by Elevation of Intracellular Ca$^{2+}$ and ROS Levels in Endothelial Cells The present inventors performed an in-situ TGase activity assay using confocal microscopy to evaluate whether VEGF can activate TGase in HRECs. It has been reported that vascular leakage in diabetic retina is predominantly caused by VEGF. VEGF increased in-situ TGase activity with increasing incubation times, with maximal activation at 2 hrs (p<0.001, FIG. 1A). VEGF-induced TGase activation was inhibited by ROS scavengers, N-acetyl cysteine (NAC) and Trolox, and Ca$^{2+}$ chelator BAPTA-AM (p<0.001, FIG. 1B), indicating that VEGF can activate TGase via elevation of intracellular ROS and Ca$^{2+}$ levels. As expected, the TGase inhibitors cystamine and MDC prevented the VEGF-induced elevation of TGase activity (p<0.001, FIG. 1B).

Figure 1C:
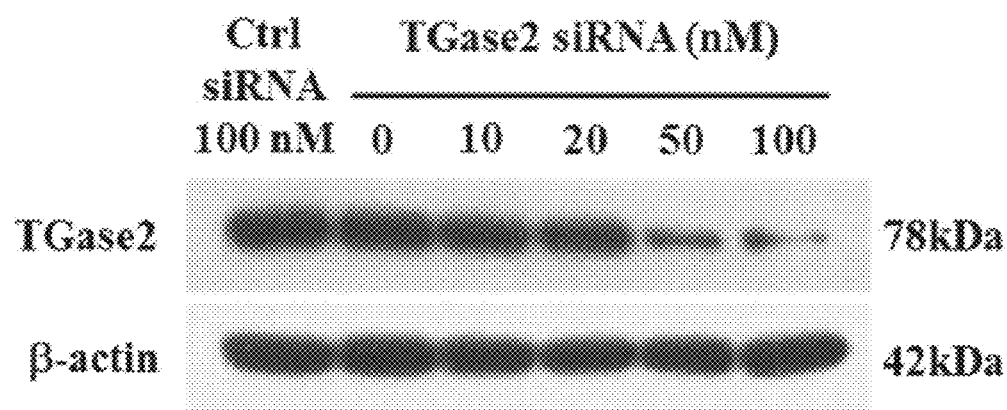
Figure 1D:
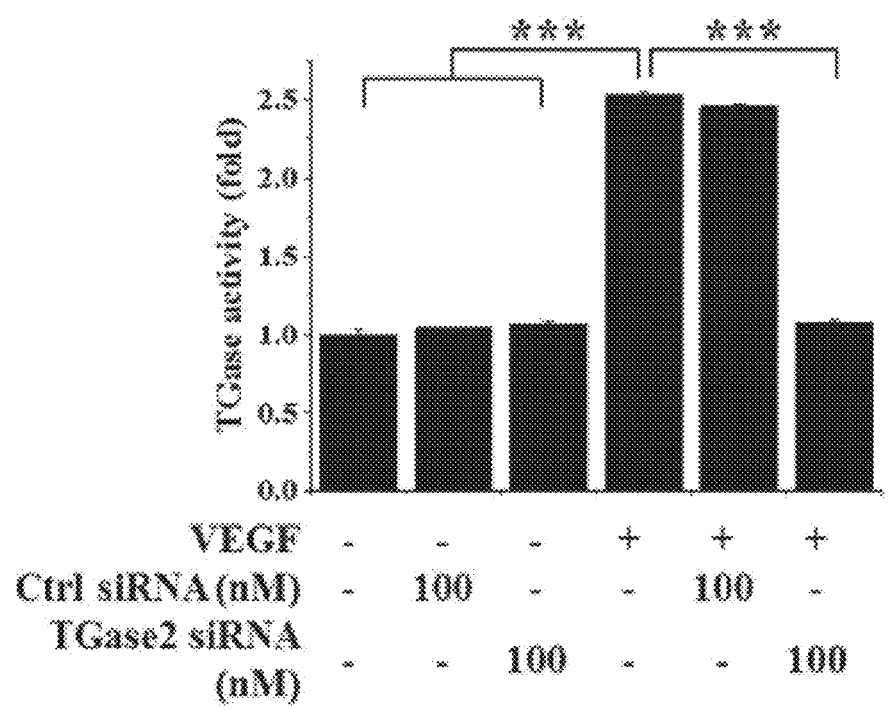

The present inventors investigated the role of TGase2 in VEGF-induced TGase2 activation by transfecting the endothelial cells with a human TGase2 siRNA. The Human TGase2 siRNA suppressed its protein expression in a dose-dependent manner, with a maximal effect at 100 nM (FIG. 1C). TGase2 siRNA completely prevented VEGF-induced TGase2 activation (p<0.001), whereas the control siRNA had no effect (FIG. 1D). TGase2 siRNA or control siRNA alone showed negligible effects on TGase activity. These results demonstrate that the greatest contribution to VEGF-induced elevation of in situ TGase activity can be attributed to TGase2, not to other members of the TGase family.

Figure 1E:
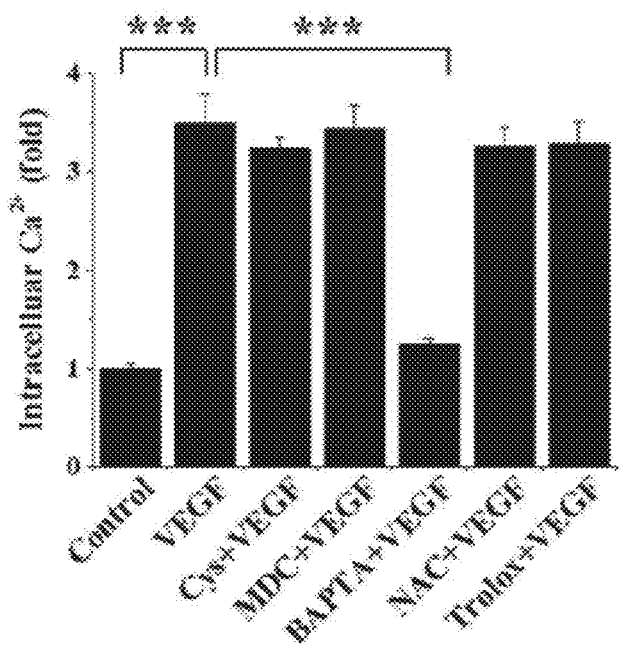

The present inventors studied the roles of intracellular ROS and Ca$^{2+}$ in VEGF-induced TGase2 activation using various inhibitors in endothelial cells. VEGF elevated intracellular Ca$^{2+}$ levels, which was inhibited by BAPTA-AM (p<0.001), but not by the ROS scavengers or the TGase inhibitors (FIG. 1E). VEGF induced intracellular ROS generation, which was significantly inhibited by the ROS scavengers or BAPTA-AM (p<0.001), but not by the TGase inhibitors (FIG. 1F), suggesting that intracellular $Ca^{2+}$ is involved in VEGF-induced ROS generation. These results elucidate that VEGF activated TGase2 via the sequential elevation of intracellular $Ca^{2+}$ and ROS levels in endothelial cells.

Figure 1F:
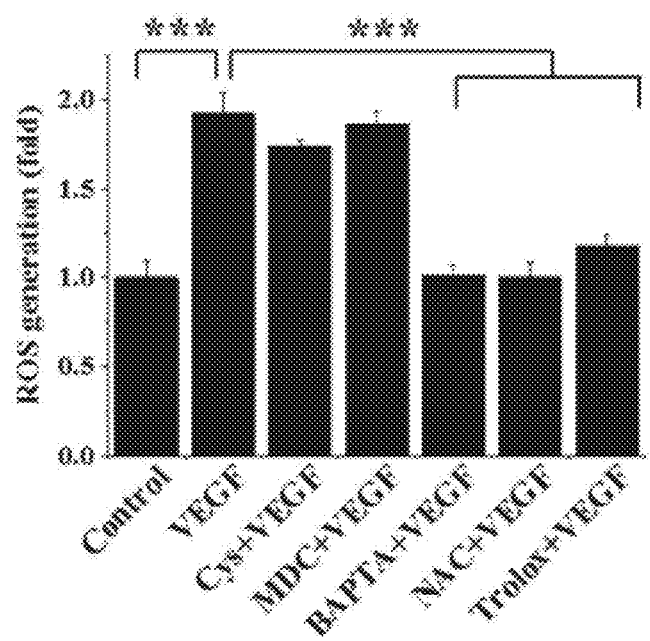

A detailed description of FIGS. 1A-1F are given below. FIGS. 1A-1F show that VEGF-induced TGase2 activation is mediated by the elevation of intracellular $Ca^{2+}$ and ROS levels in HRECs. (A, B) HRECs were incubated with 10 ng/ml VEGF for the indicated times (A) or for 2 hrs (B) in the presence of TGase inhibitors (50 µM cystamine and 20 µM MDC), 5 µM $Ca^{2+}$ chelator BAPTA-AM, or ROS scavengers (1 mM NAC or 0.5 µM Trolox). In-situ TGase activity was determined by confocal microscopy as described in Research Design and Methods (A: Time course changes in VEGF-induced transglutaminase activation; and B: Effects of various inhibitors on VEGF-induced transglutaminase activation). (C,D) HRECs were transfected with the indicated concentrations (C) or 100 nM (D) of human TGase2-specific siRNA (TGase2 siRNA) or 100 nM control (Ctrl) siRNA. Endothelial cells were treated with 10 ng/ml VEGF and subjected to confocal microscopic determination of in-situ TGase activity (C: Dose-dependent inhibition of TGase2 expression by TGase2 siRNA, TGase2 expression being analyzed by Western blot; and D: TGase2 siRNA prevention of VEGF-induced transglutaminase activation). FIGS. 1E and 1F show the effects of various inhibitors on the elevation of intracellular $Ca^{2+}$ (E) and ROS (F). Intracellular $Ca^{2+}$ and ROS levels were determined by confocal microscopy as described in Research Design and Methods. Results are expressed as mean±SD from three independent trials (***p<0.001).

Figure 2A:
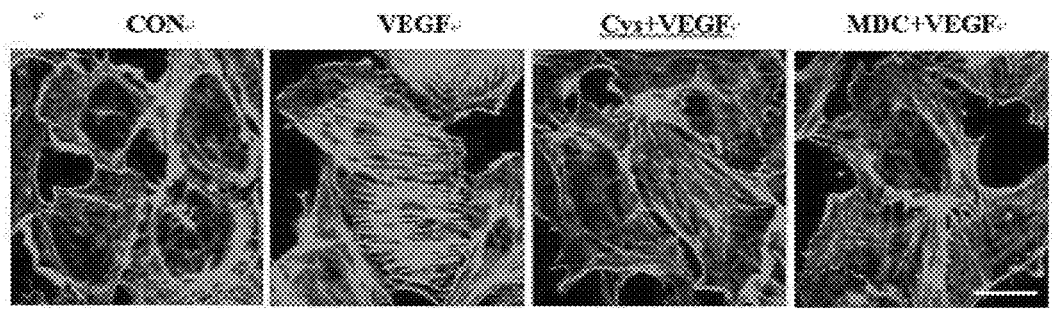
Figure 2B:
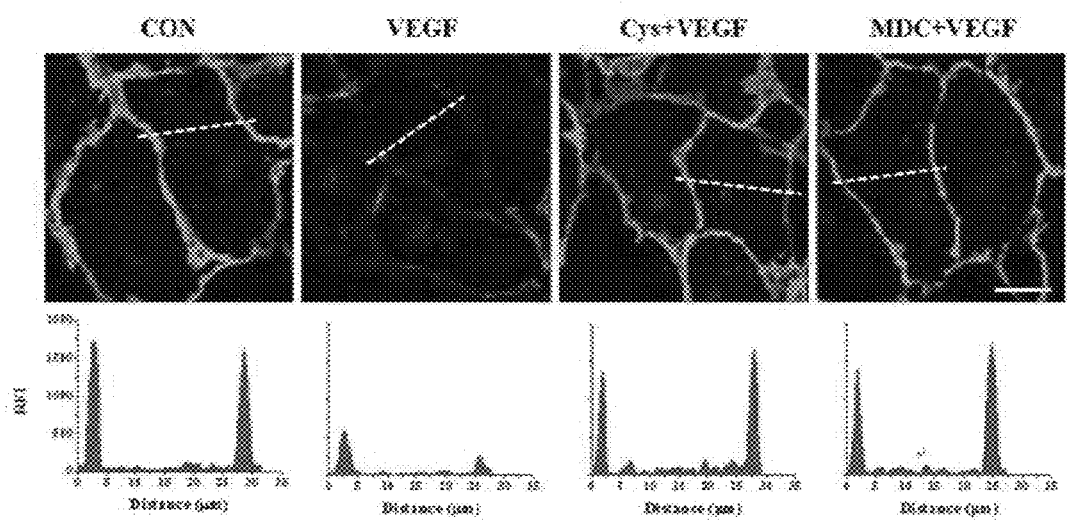
Figure 2D:
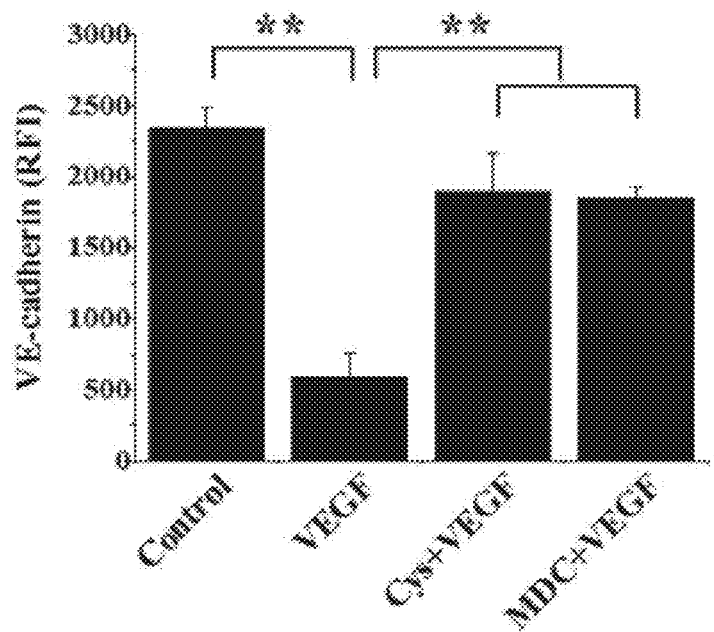
Figure 2D:
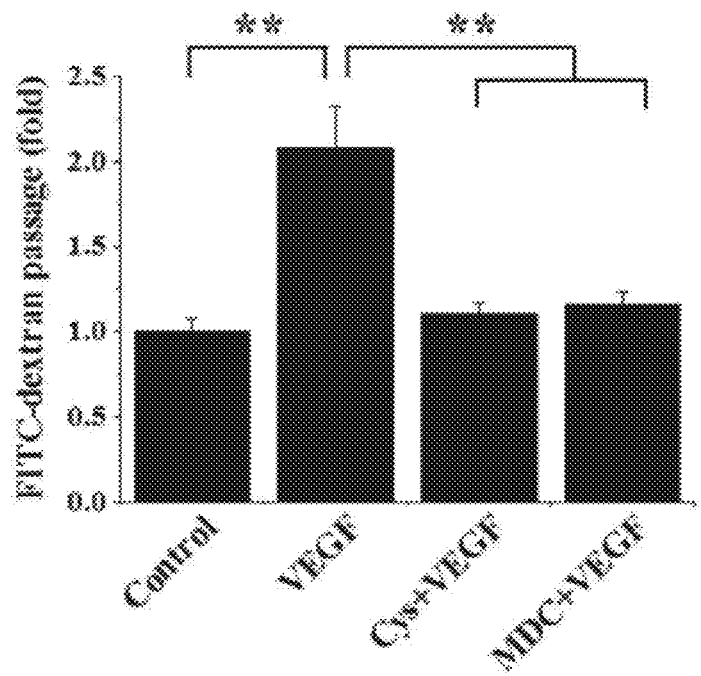

Test Example 2: Evaluation for the Role of TGase2 in VEGF-Induced Stress Fiber Formation, VE-Cadherin Disruption and Endothelial Cell Permeability To investigate the role of TGase2 in VEGF-mediated vascular leakage, the present inventors estimated the effects of cystamine and MDC on VEGF-induced stress fiber formation and adherens junction disruption in HRECs. VEGF activated stress fiber formation, which was prevented by the two TGase inhibitors (FIG. 2A). VEGF induced VE-cadherin breakdown, which was inhibited by the TGase inhibitors (FIG. 2B). The changes in stability of VE-cadherin were represented by line profiles displaying the distribution of relative fluorescence intensity, as shown by the white lines crossing two cell-cell contacts. The VE-cadherin breakdown was also quantitatively analyzed by measuring the peak fluorescence intensities of the histograms (FIG. 2C). The role of TGase2 in vascular leakage was further investigated via an in-vitro endothelial cell monolayer permeability assay using HRECs. VEGF increased in-vitro endothelial permeability, which was inhibited by the TGase inhibitors (p<0.01; FIG. 2D). Thus, it is likely that TGase2 is implicated in VEGF-induced endothelial cell permeability through stress fiber formation and VE-cadherin disruption.

Figure 3A:
FIGS. 3A-3C show that a TGase2 siRNA inhibits VEGF-induced stress fiber formation and VE-cadherin disruption.
Figure 3B:
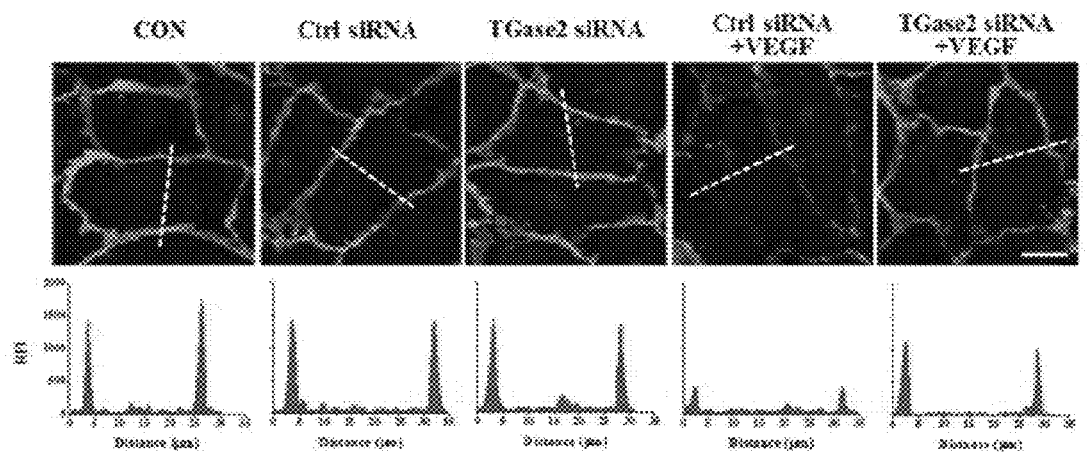
Figure 3C:
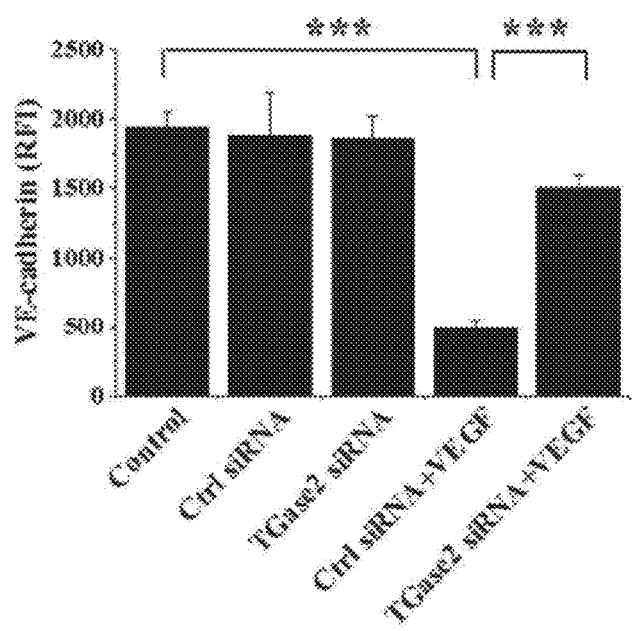

To confirm the role of TGase2 in VEGF-induced vascular leakage, the present inventors investigated the effect of human TGase2 siRNA on VEGF-induced stress fiber formation and VE-cadherin disruption in endothelial cells. Consistent with the findings in FIGS. 2A-2D, VEGF activated stress fiber formation in endothelial cells transfected with control siRNA, but not in TGase2 siRNA-treated cells (FIG. 3A). TGase2 siRNA or control siRNA alone had no significant effect on stress fiber formation. VEGF induced VE-cadherin disruption in control siRNA-treated endothelial cells, which was prevented by TGase2 siRNA transfection (p<0.001; FIGS. 3B and 3C). TGase2 siRNA or control siRNA alone had no effect on VE-cadherin disruption. Taken together, TGase2 plays a critical role in VEGF-mediated endothelial permeability through stress fiber formation and VE-cadherin disruption in endothelial cells.

Figure 4A:
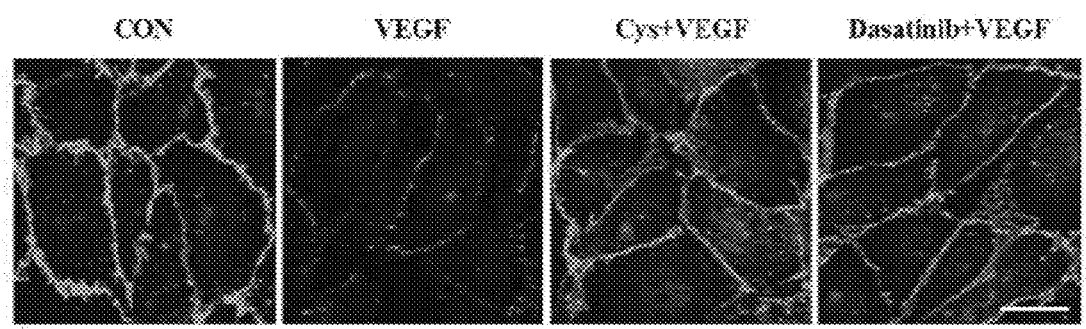
FIGS. 4A-4C show that inhibitors against TGase and cSrc prevent VEGF-induced β-catenin disruption and endothelial cell permeability.

Then, the present inventors investigated whether β-catenin and c-Src are involved in TGase2-mediated endothelial permeability in HRECs. It has been reported that TGase2 regulates β-catenin signaling through a c-Src-dependent mechanism. VEGF induced β-catenin breakdown, which was inhibited by the TGase inhibitor cystamine and the Src family kinase inhibitor dasatinib (FIG. 4A). Cystamine prevented c-Src phosphorylation ($Tyr^{416}$) induced by VEGF. Dasatinib blocked VEGF-induced c-Src phosphorylation (FIG. 4B) and endothelial permeability (FIG. 4C). These results indicate that TGase2 is involved in VEGF-induced adherens junction breakdown through a mechanism involving C-Src and β-catenin.

FIGS. 2A to 4C will be described in detail below.

FIGS. 2A-2D show that TGase inhibitors prevent VEGF-induced stress fiber formation, VE-cadherin disruption and endothelial cell monolayer permeability. (A-C) HRECs were preincubated with 50 µM cystamine (Cys) and 20 µM MDC for 30 min and treated with 10 ng/ml VEGF. Stress fibers and VE-cadherin were stained and visualized by confocal microscopy as described in Research Design and Methods (n=3) ((A) Representative images of stress fibers. Scale Bar, 30 µm. (B) Representative images of VE-cadherin. Scale Bar, 10 µm). Adherens junctions are represented by histograms of VE-cadherin as indicated by dotted lines. (C) Adherens junctions were quantitatively analyzed using the peak fluorescence intensities of the histograms at the single-cell level. The results are expressed as mean±SD from three independent trials. (D) In-vitro endothelial cell monolayer permeability assay. HRECs on inserts of Transwell® Permeable Supports were incubated with 50 µM cystamine and 20 µM MDC for 30 min and treated with 10 ng/mL VEGF for 90 min. The amount of FITC-dextran that diffused to the lower chamber was measured by a microplate spectrofluorometer (n=3) (**p<0.01).

FIGS. 3A-3C show that a TGase2 siRNA inhibits VEGF-induced stress fiber formation and VE-cadherin disruption. HRECs were transfected with 100 nM human TGase2-specific siRNA (TGase2 siRNA) or 100 nM control (Ctrl) siRNA. Endothelial cells were treated with 10 ng/ml VEGF and subjected to the confocal microscopic visualization of stress fibers (A) and VE-cadherin (B), as described in Research Design and Methods (n=3). (A) TGase2 siRNA inhibition of VEGF-induced formation of stress fibers. Scale bar, 30 µm. (B) Representative images of VE-cadherin and adherens junctions represented by VE-cadherin histograms. Scale bar, 10 µm. (C) Adherens junctions were quantitatively analyzed using peak fluorescence intensities of the histograms at the single-cell level. Results are expressed as mean±SD from three independent experiments (***p<0.001).

Figure 4B:
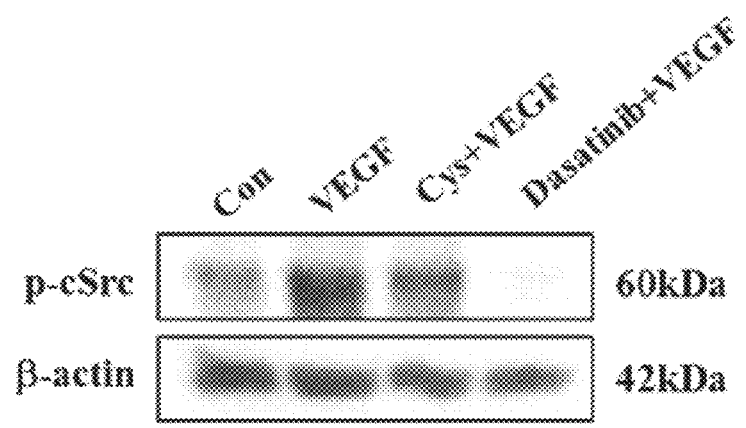
Figure 4C:
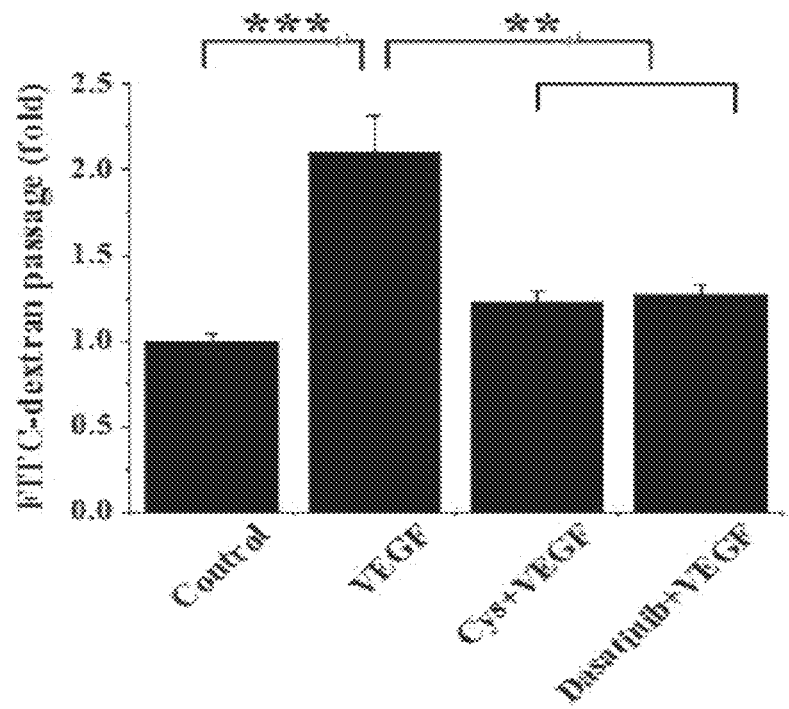

FIGS. 4A-4C show that inhibitors against TGase2 and cSrc prevent VEGF-induced β-catenin disruption and endothelial cell permeability. HRECs were preincubated with 50 µM cystamine (Cys) or 100 nM dasatinib for 30 min and treated with 10 ng/ml VEGF for 15 min (B) or 90 min (A,C). (A) β-catenin was visualized by confocal microscopy. Scale bar, 30 µm. (B) cSrc phosphorylation at $Tyr^{416}$ was analyzed by Western blot. (C) In-vitro endothelial cell monolayer permeability assay. Results are expressed as mean±SD from three independent experiments (p<0.01, *p<0.001).

Test Example 3: Evaluation Whether Hyperglycemia Induces Vascular Leakage by Activating TGase2 in the Diabetic Retina To validate the in-vitro findings, the present inventors further investigated the role of TGase2 in hyperglycemia-induced vascular leakage in the retina of diabetic mice. For this study, the present inventors designed an in-vivo TGase activity assay using confocal microscopy in mouse retina (FIG. 5A). In this assay, BAPA, which is a TGase2 pseudo substrate, was systemically delivered into the blood circulatory system by injection into the left ventricles of mice, and biotinylated proteins in the retinas were probed with FITC-conjugated streptavidin.

Figure 5B:
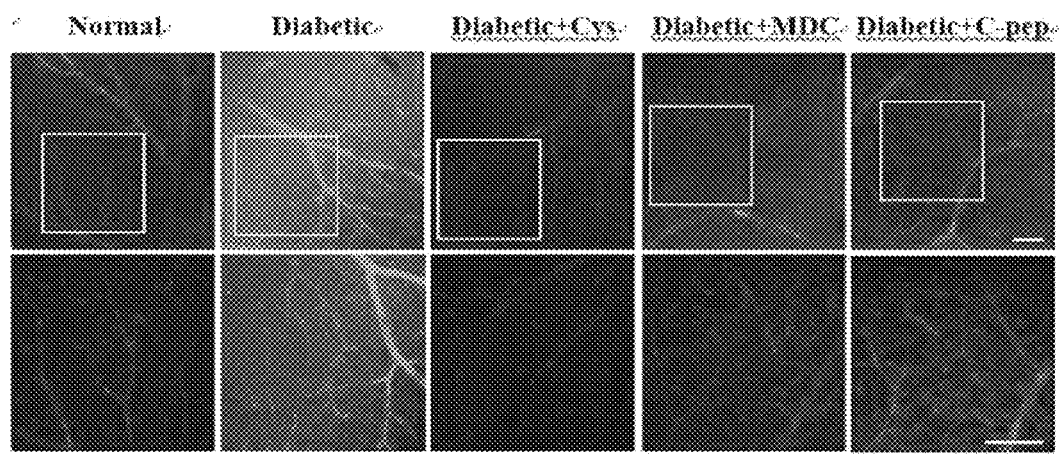
Figure 5C:
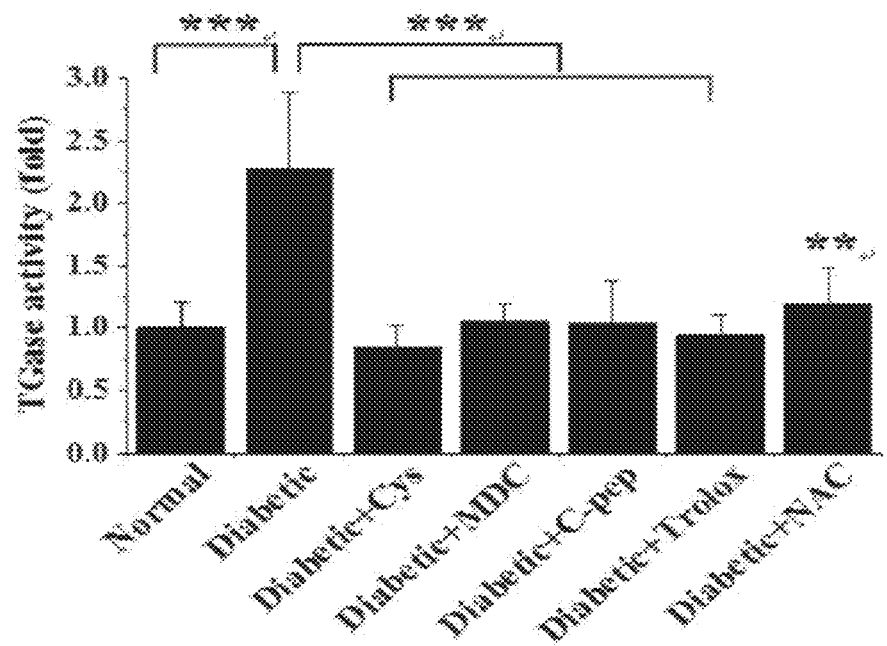
Figure 10A:
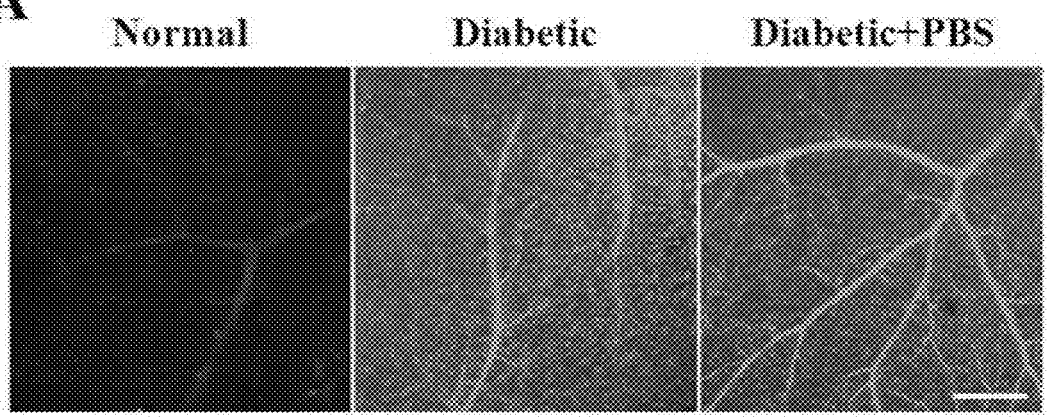
FIG. 10A shows the in-vivo TGase activity in retinal blood vessels of normal and streptozotocin-induced diabetic mice.
Figure 10B:
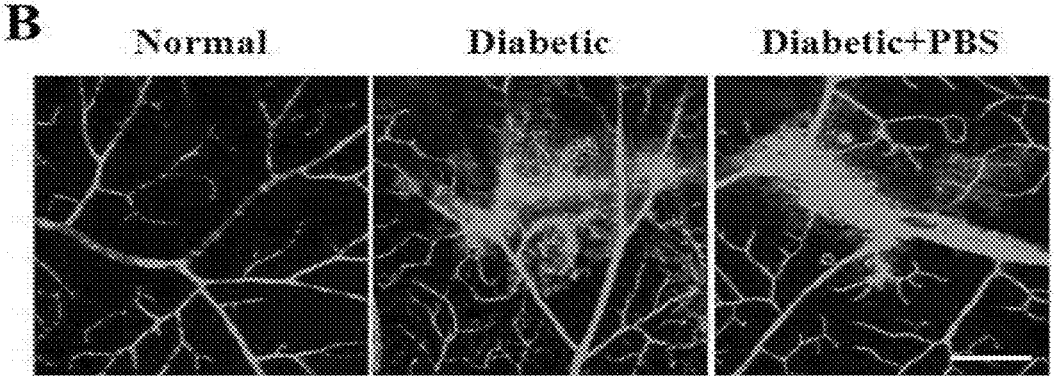
FIG. 10B shows the evaluation for the extravasation of FITC-dextran in normal and streptozotocin-induced diabetic mice, in which PBS was injected into the contralateral eye of diabetic mice (Scale bar, 150 μm)

In-vivo TGase activity was highly elevated in the blood vessels and ganglion cells of streptozotocin-diabetic mouse retina compared to the normal retina (n=8) and this hyperglycemia-induced TGase2 activation was suppressed by intravitreal injection of the TGase inhibitors cystamine and MDC (FIG. 5B and FIGS. 10A-10B). Then, the present inventors quantitatively analyzed in-vivo TGase activity by determining the fluorescence intensities of FITC-conjugated streptavidin in retina tissues. The average TGase2 activity in the retinas of diabetic mice was approximately twice as high as that of normal mice (p<0.001, n=8; FIG. 5C). The TGase inhibitors reversed the hyperglycemia-induced elevation of TGase2 activity in the blood vessels and ganglion cells of diabetic retinas (p<0.001, n=8; FIG. 5C). These results demonstrate that our in-vivo confocal microscopic assay successfully analyzed TGase2 activation by hyperglycemia in diabetic retina.

Figure 6A:
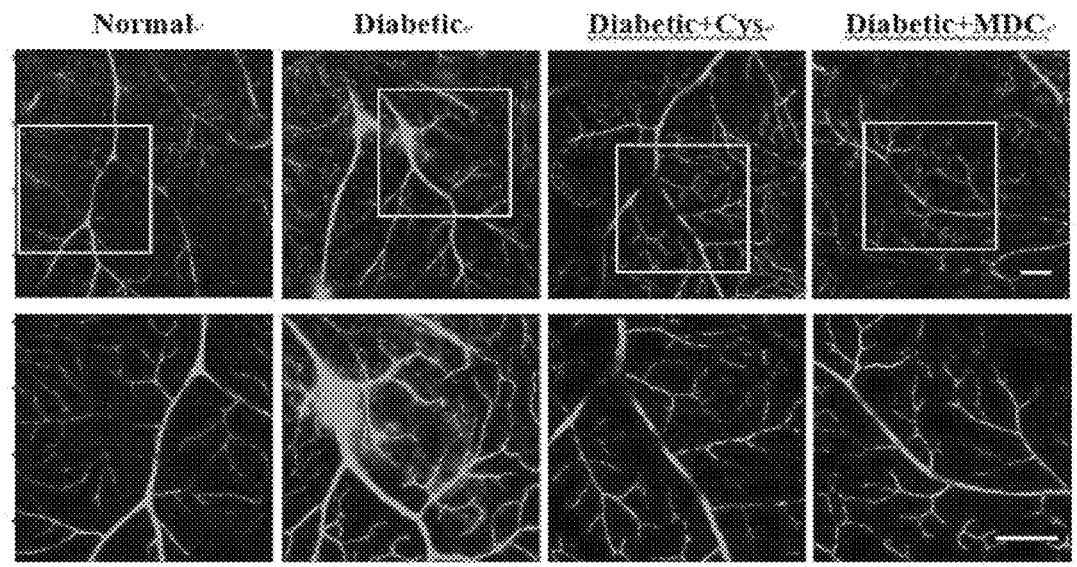
FIGS. 6A-6D show that the intravitreal injection of TGase inhibitors prevents vascular leakage in the retinas of diabetic mice.
Figure 6B:
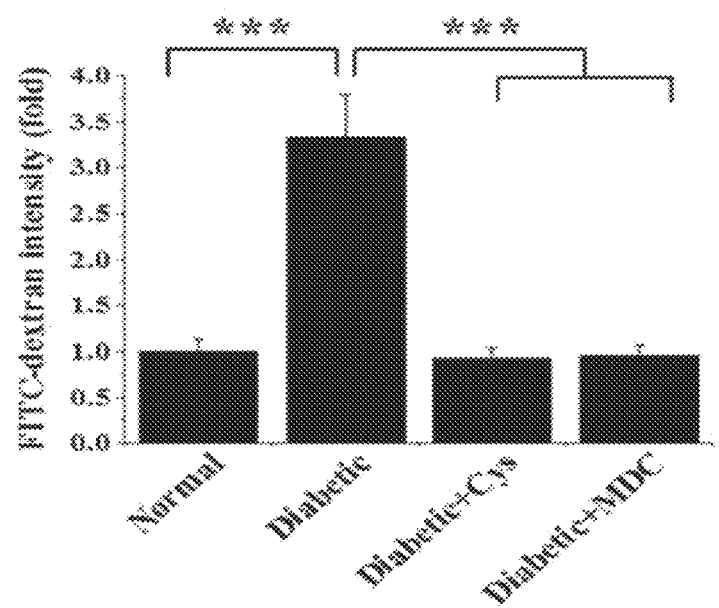

Next, the present inventors investigated the role of TGase2 in vascular leakage in the diabetic retina by fluorescence angiography after the intravitreal injection of cystamine and MDC into mouse eyes. High levels of extravasation of FITC-dextran were observed in the retinas of diabetic mice, but this leakage was blocked in the retinas of the contralateral eyes injected with the TGase inhibitors (FIG. 6A and FIGS. 10A-10B). Fluorescence intensity in the retina of diabetic mice was approximately 3 times as high as that in control mice (p<0.001, n=8); however, cystamine and MDC prevented vascular leakage (p<0.001, n=8, FIG. 6B). These results indicate that hyperglycemia induces vascular leakage by activating TGase2 in the retina of diabetic mice.

Figure 6C:
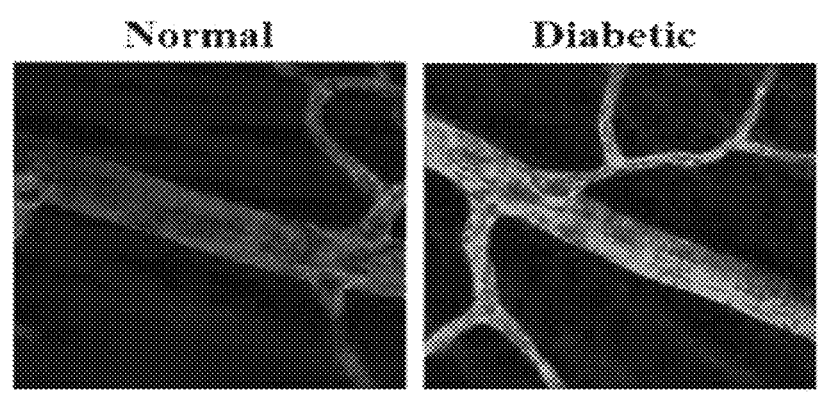
Figure 6D:
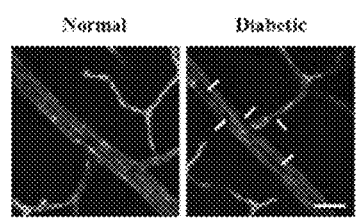

The present inventors investigated whether hyperglycemia can induce stress fiber formation and adherens junction breakdown in diabetic retina. Consistent with the in-vitro findings, actin filament staining showed the enhanced formation of stress fibers in diabetic retina compared with the control (FIG. 6C). The VE-cadherin staining showed continuous VE-cadherin distribution along the junctions in the control, but exhibited frequent disrupted adherens junctions in diabetic retina (FIG. 6D). These results elucidate that hyperglycemia induces vascular leakage by stress fiber formation and adherens junction disruption in the retina of diabetic mice.

FIGS. 5A-5C and 6A-6D will be described in detail below.

FIGS. 5A-5C show that in-vivo TGase activity is elevated in the retinas of diabetic mice and is inhibited by intravitreal injection of C-peptide and various inhibitors. (A) A schematic diagram for determining TGase2 activity in mouse retina. (B,C) Streptozotocin-induced diabetic mice were intravitreally injected with 2 µl cystamine (diabetic+Cys), MDC (diabetic+MDC), C-peptide (diabetic+C-pep), Trolox (diabetic+Trolox) or NAC (diabetic+NAC) into one eye and an equal volume of PBS into the contralateral eye (diabetic). Non-diabetic mice were also intravitreally injected with 2 µl PBS into both eyes (normal). TGase2 activities in retinas were visualized by confocal microscopy and quantitatively determined as described in Research Design and Methods (n=8 per group). (B) Representative TGase activity images in the retinas. The square areas are displayed as magnified images at the bottom of each image. Scale bar, 100 m. (C) In-vivo TGase activities were quantified by measuring the fluorescence intensity in retinas (***p<0.001).

FIGS. 6A-6D show that the intravitreal injection of TGase inhibitors prevents vascular leakage in the retinas of diabetic mice. (A, B) Streptozotocin-diabetic mice were intravitreally injected with PBS (diabetic), cystamine (diabetic+Cys) or MDC (diabetic+MDC) into the eyes. Non-diabetic mice were also intravitreally injected with PBS into eyes (normal). Vascular leakage in retinas was visualized by confocal microscopy as described in Research Design and Methods (n=8 per group). (A) Representative fluorescent images of the retinas. The square areas are displayed as magnified images at the bottom of each image. Scale bar, 150 µm. (B) Retina permeability was quantified by measuring the fluorescence intensities of FITC-dextran in (A). (C,D) Stress fibers and VE-cadherin were visualized by confocal microscopy in the retinas of normal and diabetic mice (n=6 per group) as described in Research Design and Methods. (C) Representative images of stress fibers. Scale bar, 50 µm. (D) Representative images of VE-cadherin. Arrows indicate disrupted adherens junctions. Scale bar, 50 µm (***p<0.001).

Test Example 4: Evaluation of Whether TGase is Activated by VEGF-Induced ROS Generation in the Diabetic Retina The present inventors examined the effect of the ROS scavengers Trolox and NAC on hyperglycemia-induced TGase activation in the diabetic retina. Trolox prevented hyperglycemia-induced TGase2 activation in the diabetic retina (p<0.001; FIG. 5C), which is consistent with the in-vitro results shown in FIG. 1B. A similar inhibitory effect was observed by NAC (p<0.01; FIG. 5C). The role of intracellular ROS in the hyperglycemia-induced TGase2 activation was further studied using C-peptide, because C-peptide prevents vascular permeability by inhibiting VEGF-stimulated ROS generation in the diabetic retina. Human C-peptide is a 31-amino acid peptide that is released from β-cells into the peripheral circulatory system in equimolar concentrations with insulin. Intravitreal injection of the C-peptide blocked TGase2 activation in the diabetic retina (p<0.001; FIGS. 5B and 5C). Considering the role of intracellular ROS in VEGF-mediated vascular leakage in the diabetic retina, these results suggest that TGase2 is activated by VEGF-increased intracellular ROS in the diabetic retina.

Test Example 5: Evaluation of Whether Intravitreal Injection of TGase2 siRNA Inhibits TGase Activation, Vascular Leakage and TGase2 Expression in the Retinas of Diabetic Mice To confirm the role of TGase2 in vascular permeability in the diabetic retina, diabetic mice were intravitreally injected with mouse TGase2-specific siRNA and subjected to analysis of in-vivo TGase activity and vascular leakage in retinas. In-vivo TGase activity was significantly higher in the diabetic retina injected with control siRNA compared to the normal retina (p<0.001, n=8), which was blocked in the retinas of the TGase2 siRNA-injected contralateral eyes (p<0.001, n=8, FIG. 7A), demonstrating that the greatest contribution to hyperglycemia-induced TGase activation in the diabetic retina was from TGase2. Then, the present inventors analyzed the effect of TGase2 siRNA intravitreal injection on hyperglycemia-induced vascular leakage in the diabetic retina. Vascular leakage was apparent in the diabetic retina injected with control siRNA compared to the normal retina (p<0.001, n=8), which was blocked in the retinas of the TGase2 siRNA-injected contralateral eyes (p<0.01, n=8, FIG. 7B). TGase2 was expressed in all layers of the retina while being expressed at higher levels in the ganglion cell and inner plexiform layers, and its expression was significantly suppressed by TGase2 siRNA (FIG. 7C). These results demonstrate that TGase2 plays a key role in hyperglycemia-induced vascular leakage in the diabetic retina.

Figure 7A:
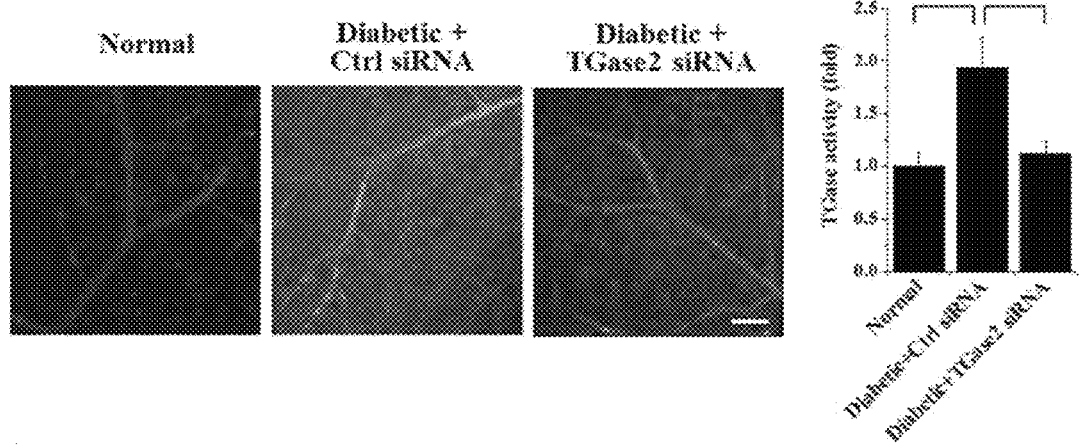
FIGS. 7A-7C show that the intravitreal injection of TGase2 siRNA prevents in vivo TGase activation, vascular leakage and TGase2 expression in the retinas of diabetic mice.
Figure 7B:
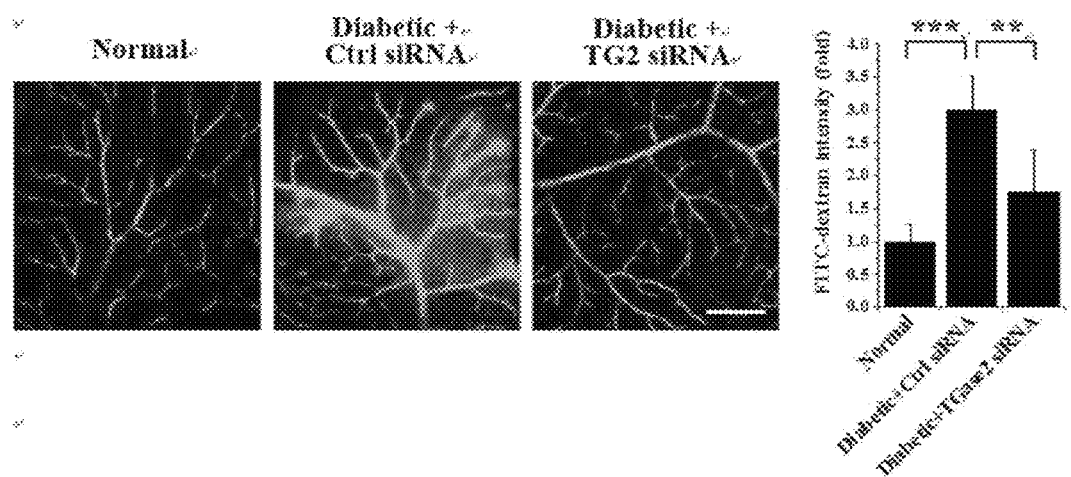
Figure 7C:
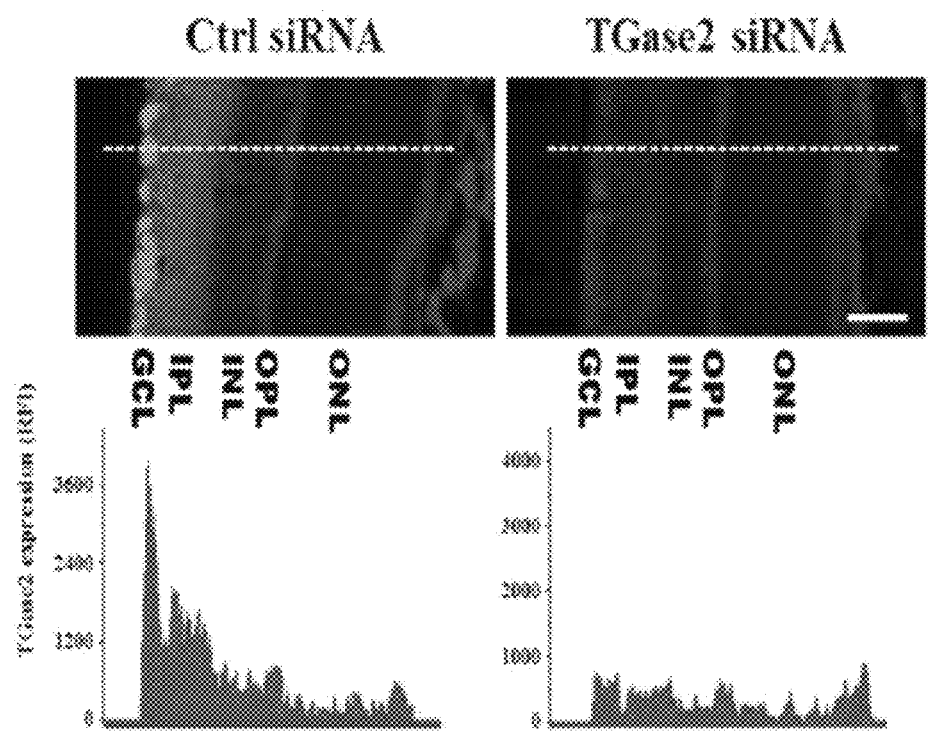

FIGS. 7A-7C will be described in detail below.

FIGS. 7A-7C show that the intravitreal injection of TGase2 siRNA prevents in-vivo TGase activation, vascular leakage and TGase2 expression in the retinas of diabetic mice. (A,B) Diabetic mice were intravitreally injected with control or TGase2-specific siRNA into the eyes. Non-diabetic mice were also intravitreally injected with control siRNA into the eyes. In-vivo TGase activity and vascular leakage in the retinas were visualized by confocal microscopy and quantitatively determined as described in Research Design and Methods (n=8 per group). (A) In-vivo TGase activity. Scale bar, 100 μm. (B) Vascular leakage. Scale bar, 150 μm. (C) Representative images of TGase2 expression in retinal cross-sections (n=4). Scale bar, 50 μm. Expression levels are represented by histograms as indicated by dotted lines (GLC, ganglion cell layer; IPL, inner plexiform layer; INL, inner nuclear layer; OPL, outer plexiform layer; p<0.01, *p<0.001).

Figure 8A:
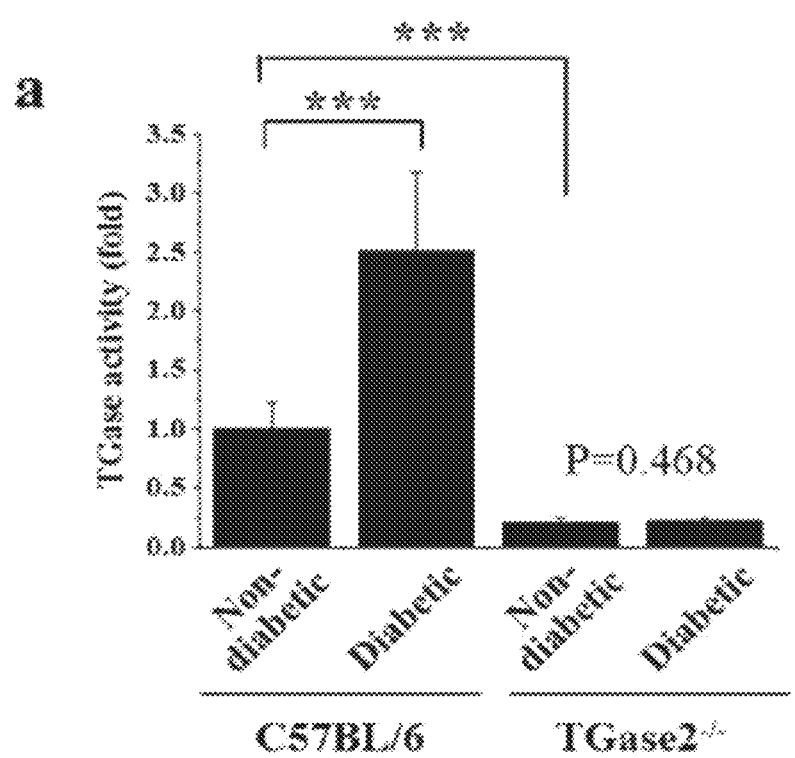
FIGS. 8A-8D show that TGase2 activation and vascular leakage were not observed in the retina of diabetic TGase2$^{-/-}$ mice and a schematic diagram for the role of TGase2 in diabetic retinopathy.
Figure 8B:
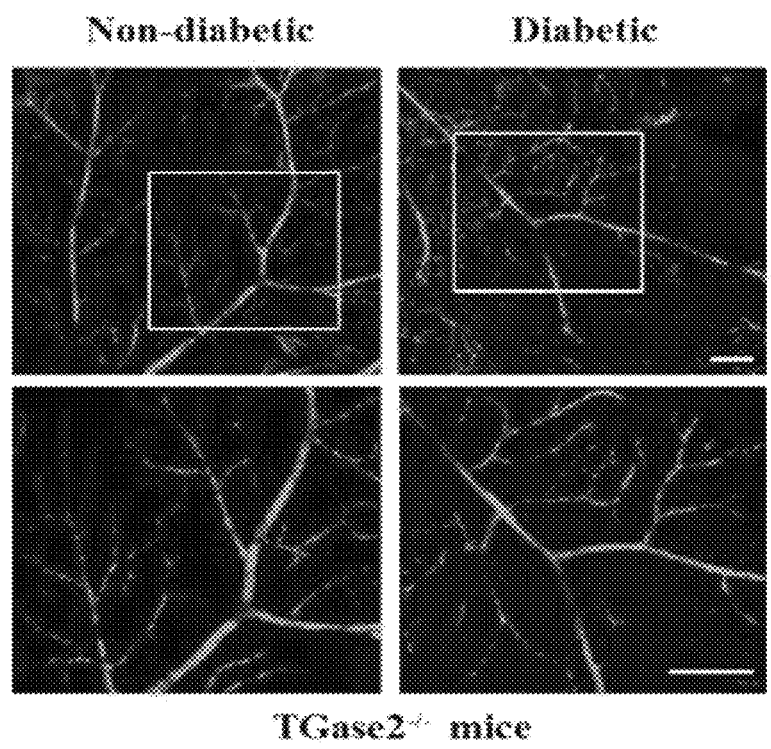
Figure 8C:
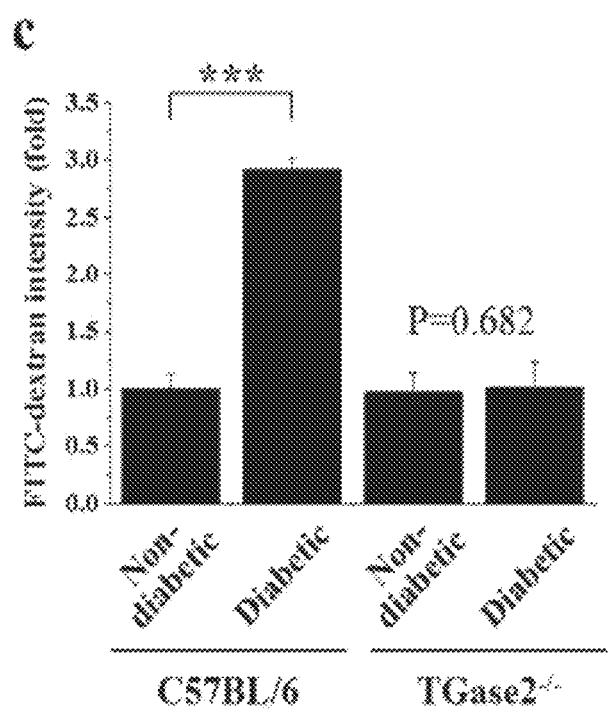

Test Example 6: Evaluation for TGase2 Activation and Vascular Leakage in the Retina of Diabetic TGase2$^{-/-}$ Mice To further confirm the role of TGase2 in vascular leakage in the diabetic retina, in-vivo TGase activity and vascular leakage were determined in the retinas of C57BL/6 and TGase2$^{-/-}$ mice at two weeks (n=8). TGase activity dramatically decreased in the retinas of non-diabetic TGase2$^{-/-}$ mice compared to non-diabetic C57BL/6 mice (p<0.001) and this decreased TGase activity was not changed by hyperglycemia in the diabetic TGase2$^{-/-}$ mice (p=0.468). As expected, TGase activity was elevated in diabetic C57BL/6 mice (p<0.001), confirming that the greatest contribution to TGase activation in the diabetic retina was made by TGase2. Then, the present inventors investigated vascular leakage in the retinas of non-diabetic and diabetic TGase2$^{-/-}$ mice (n=8). Vascular leakage was not induced in the retinas of diabetic TGase2$^{-/-}$ mice compared to the non-diabetic TGase2$^{-/-}$ mice (p=0.682, n=8; FIGS. 8B and 8C), which is consistent with the in-vivo experiments using intravitreal injection of TGase2 siRNA in FIGS. 7A-7C. Vascular leakage was also undetectable in the retina of diabetic TGase2$^{-/-}$ mice at 4 weeks (data not shown). These findings demonstrate that intracellular ROS-induced TGase2 activation plays a key role in VEGF-mediated vascular leakage in the diabetic retina.

FIGS. 8A-8D will be described in detail below.

FIGS. 8A-8D show that TGase2 activation and vascular leakage were not observed in the retina of diabetic TGase2$^{-/-}$ mice and a schematic diagram for the role of TGase2 in diabetic retinopathy. (A-C) In-vivo TGase activity and vascular leakage in the retinas of non-diabetic and diabetic C57BL/6 mice and non-diabetic and diabetic TGase2$^{-/-}$ mice were visualized by confocal microscopy and quantitatively determined as described in Research Design and Methods (n=8 per group). (A) No TGase2 activation in the retinas of diabetic TGase2$^{-/-}$ mice. (B) Representative fluorescent images of FITC-dextran in the retinas of non-diabetic and diabetic TGase2$^{-/-}$ mice. Scale bar, 150 μm. (C) No vascular leakage in the retinas of diabetic TGase2$^{-/-}$ mice. (D) A proposed model depicting the role of TGase2 in VEGF-induced vascular leakage in the diabetic retina.

Figure 12A:
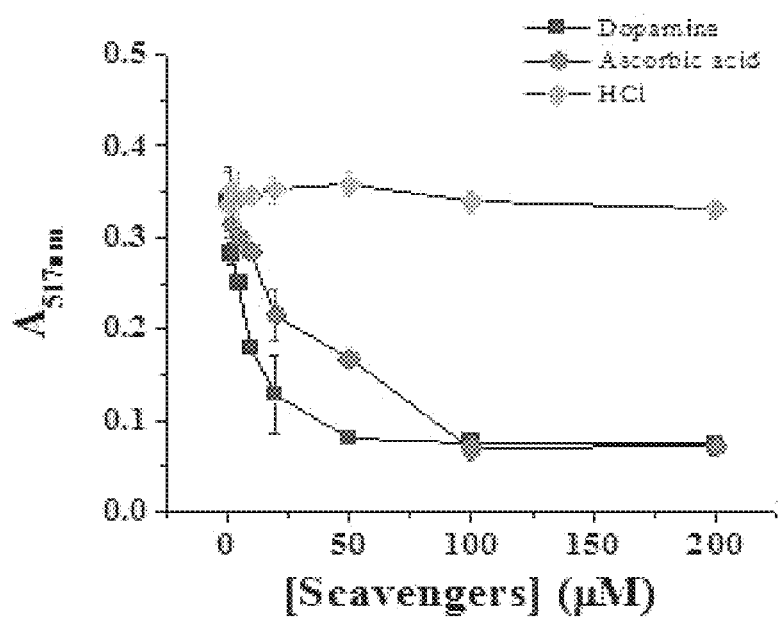
FIG. 12A shows the DPPH radical scavenging activity of dopamine.
Figure 12B:
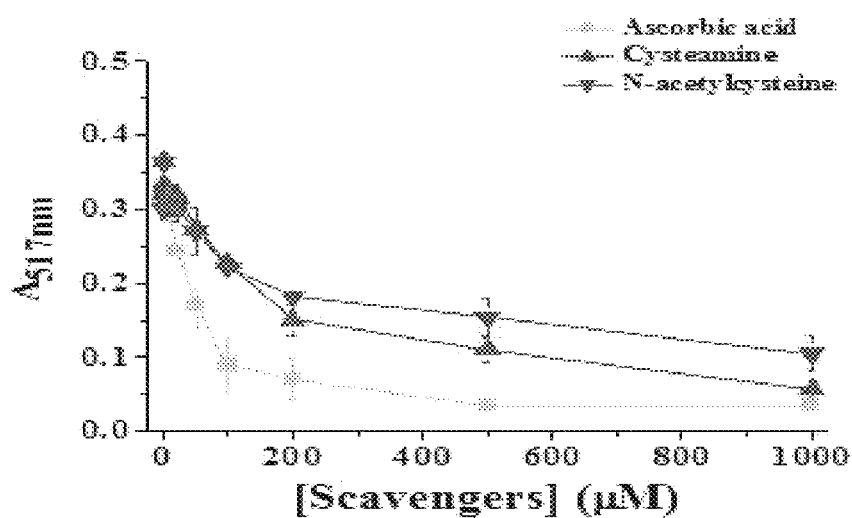
FIG. 12B shows the DPPH radical scavenging activity of cysteamine.
Figure 12C:
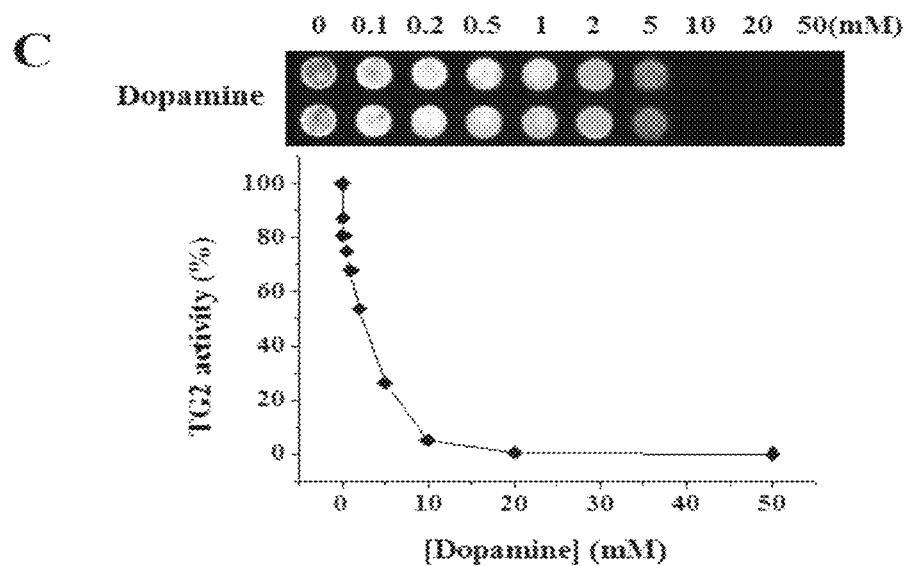
FIG. 12C shows the inhibitory effect of dopamine against TGase2 activity in a dose-dependent manner.
Figure 12D:
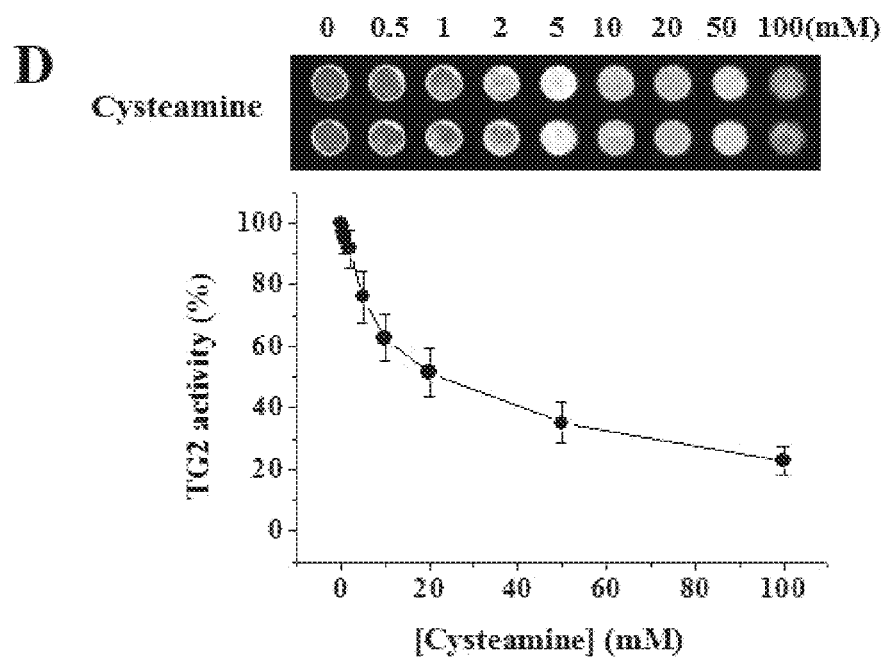
FIG. 12D shows the inhibitory effect of cysteamine against TGase2 activity in a dose-dependent manner.
Figure 13A:
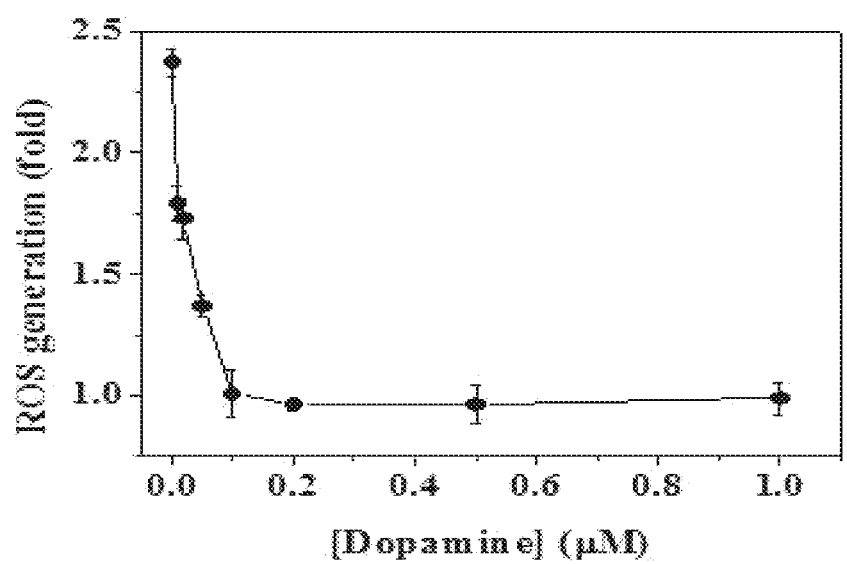
FIG. 13A shows the inhibitory effect of dopamine on VEGF-induced ROS generation in HUVECs.
Figure 13B:
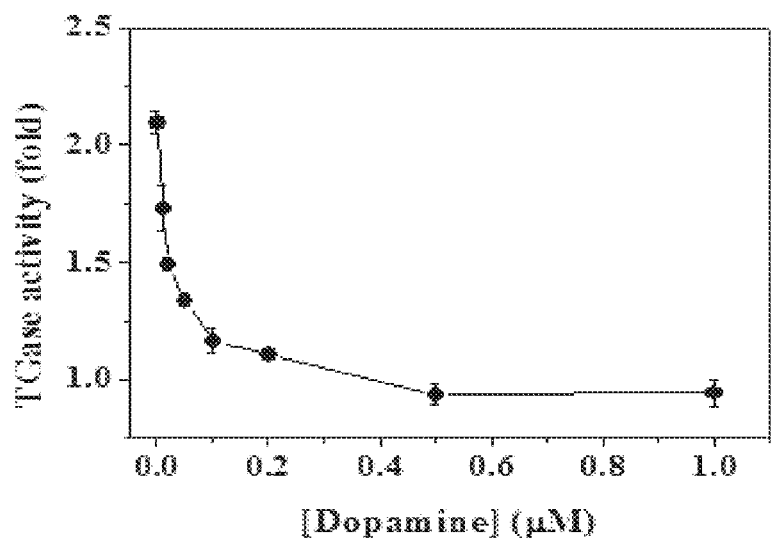
FIG. 13B shows the inhibitory effect of dopamine on TGase activity in HUVECs.
Figure 13C:
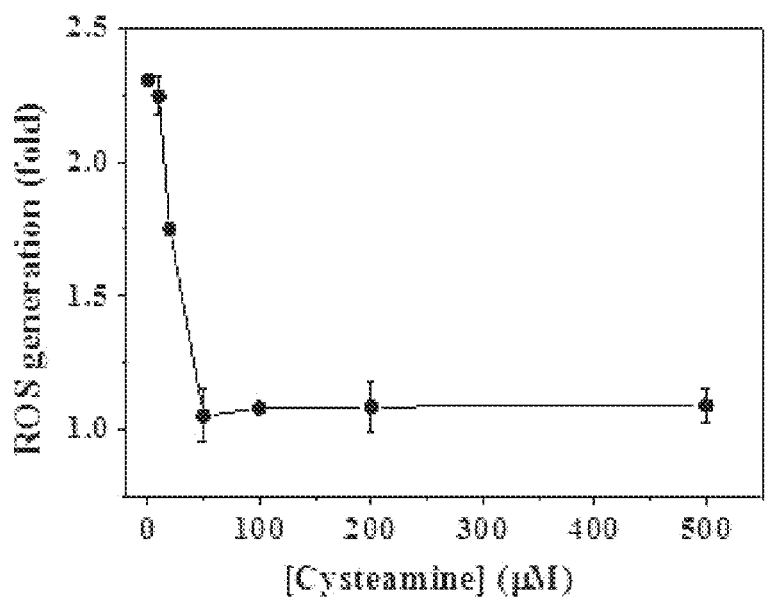
FIG. 13C shows the inhibitory effect of cysteamine on VEGF-induced ROS generation in HUVECs.
Figure 13D:
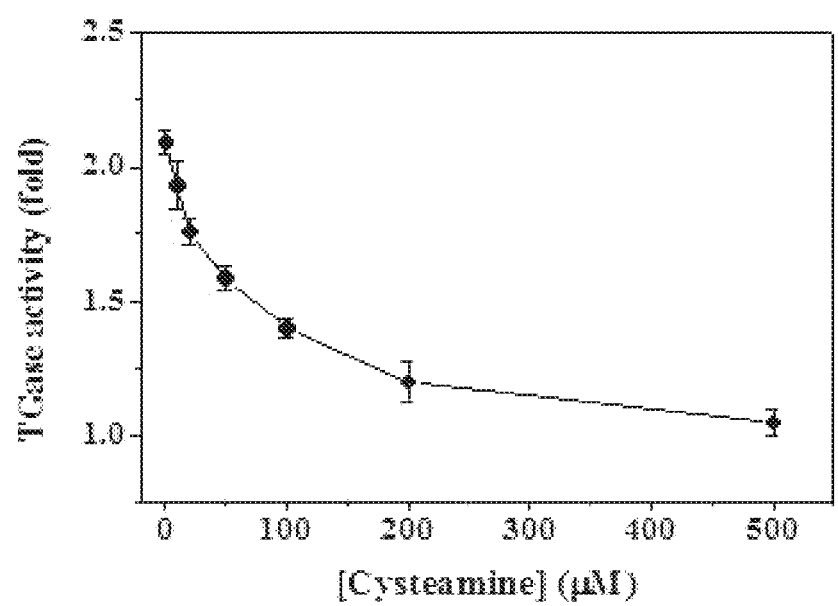
FIG. 13D shows the inhibitory effect of cysteamine on TGase TGase activity in HUVECs.

Test Example 7: In-Vitro Assay for the Antioxidant and TGase Inhibitory Effects of Dopamine and Cysteamine Dopamine and cysteamine were evaluated for antioxidant activity and an inhibitory effect against TGase activity by DPPH radical scavenging activity analysis and protein chip-based TGase activity analysis. Dopamine and cysteamine exhibited an antioxidant effect similar to those of N-acetyl cysteine (NAC) and ascorbic acid, which are known as ROS scavengers (FIGS. 12A and 12B). Also, both dopamine and cysteamine inhibited TGase2 activity in a dose-dependent manner (FIGS. 12C and 12D). These results indicate that dopamine and cysteamine have antioxidant activity as well as an inhibitory effect against TGase.

Test Example 8: Evaluation for Inhibition of VEGF-Induced ROS Generation and TGase2 Activation by Dopamine and Cysteamine in HUVECs Dopamine and cysteamine were investigated to determine whether they are able to prevent VEGF-induced ROS generation and TGase activation in HUVECs. VEGF enhanced ROS generation and TGase activation in HUVECs, which were inhibited by dopamine and cysteamine (FIGS. 13A to 13D). These findings indicate that dopamine and cysteamine have an inhibitory effect on VEGF-induced ROS generation and TGase activation.

Figure 14:
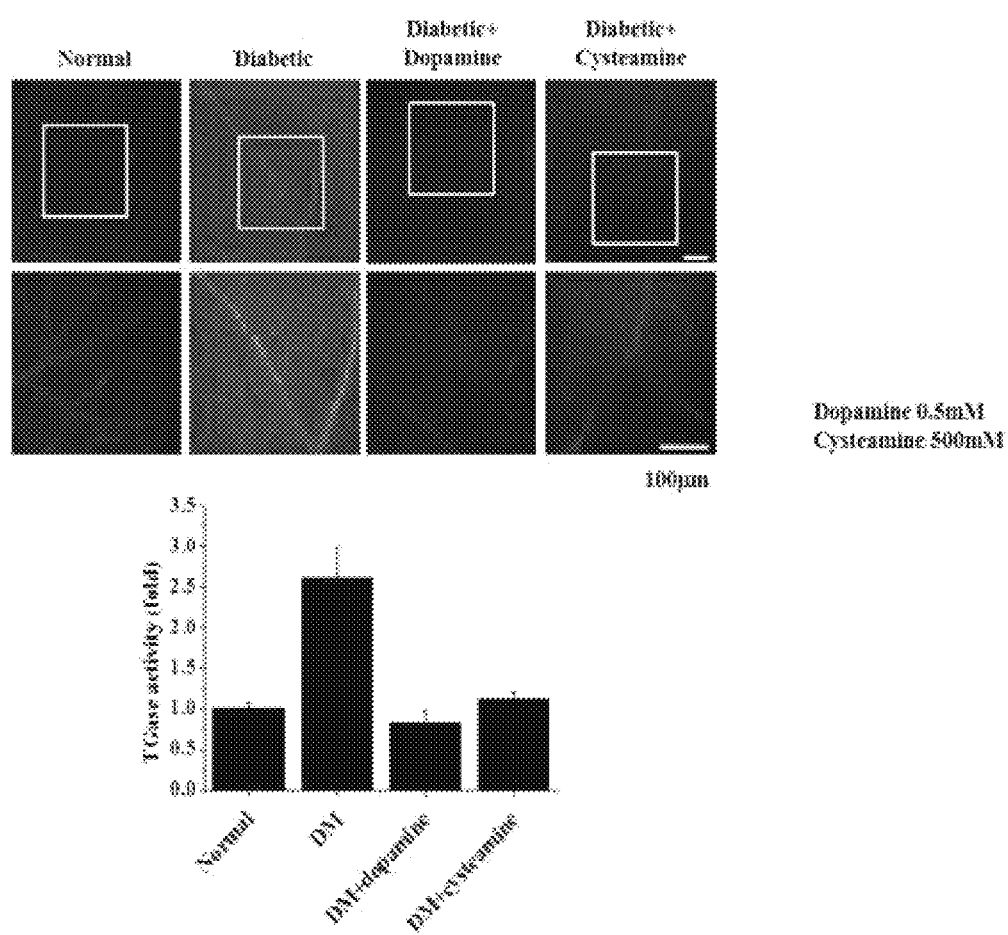
FIG. 14 shows the in-vivo inhibitory effect of intravitreal injection of dopamine and cysteamine on TGase2 activity in the retinas of diabetic mice.

Test Example 9: Evaluation of Whether Intravitreal Injection of Dopamine and Cysteamine Inhibits Elevation of TGase Activity in the Retinas of Diabetic Mice In order to confirm the in-vitro results, TGase activity was quantitatively analyzed by visualizing the activity of TGase in the mouse retina and measuring fluorescence intensity using a confocal microscope. Dopamine and cysteamine were intravitreally injected at concentrations of 0.5 mM and 500 mM, respectively. TGase activity in the retinas of diabetic mice was markedly increased compared to that in normal mouse retinas, and the increase was inhibited by the intravitreal injection of dopamine and cysteamine (FIG. 14).

Figure 15:
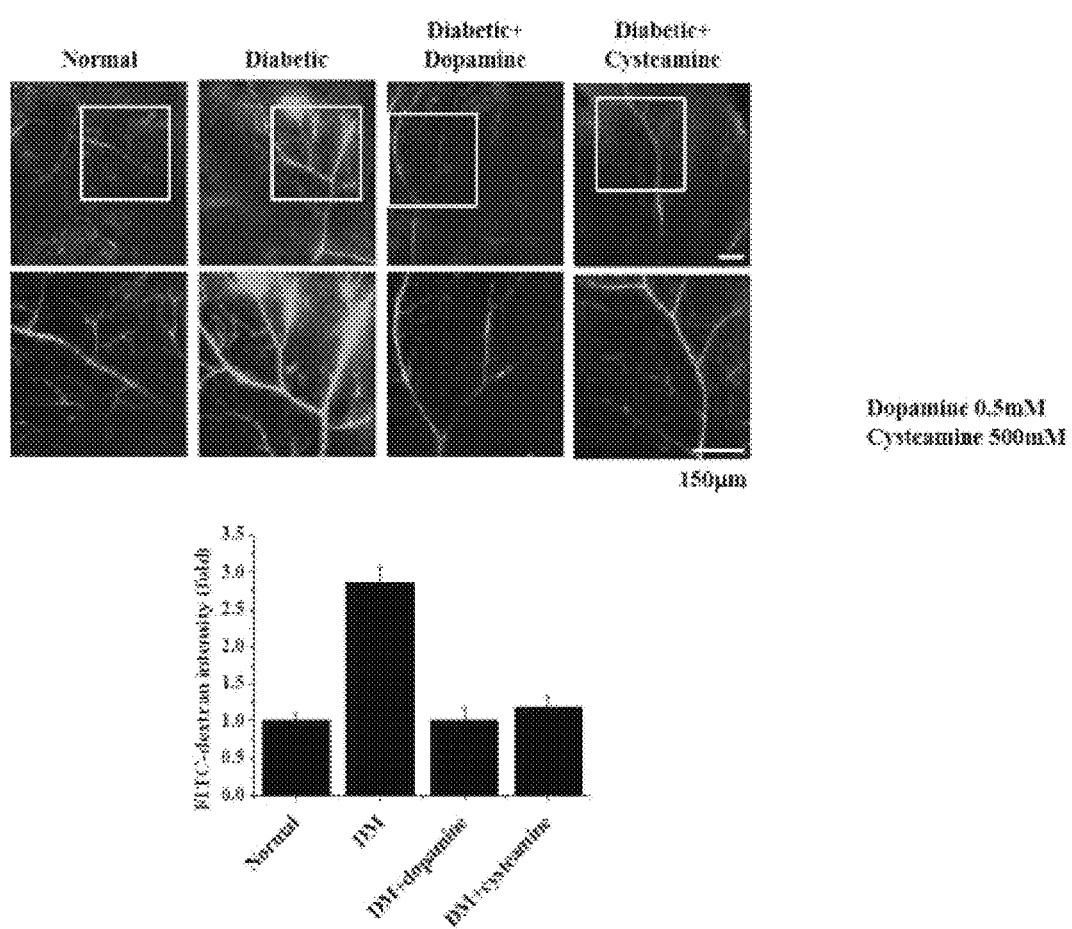
FIG. 15 shows the inhibitory effect of intravitreal injection of dopamine and cysteamine on vascular leakage in the retinas of diabetic mice.

Test Example 10: Evaluation of Whether Intravitreal Injection of Dopamine and Cysteamine Inhibits Vascular Leakage in Diabetic Retinas Dopamine and cysteamine were intravitreally injected into mouse eyes, and diabetic retinas were then analyzed for vascular leakage through fluorescein angiography. Vascular leakage in the retinas of diabetic mice was markedly increased compared to that in normal retinas (n=6), and the increase was inhibited by the intravitreal injection of 0.5 mM dopamine and 500 mM cysteamine (FIG. 15).

The in-vivo studies in Test Examples 9 and 10 demonstrated that dopamine and cysteamine effectively prevent TGase activation and vascular leakage in diabetic retinas.

Figure 8D:
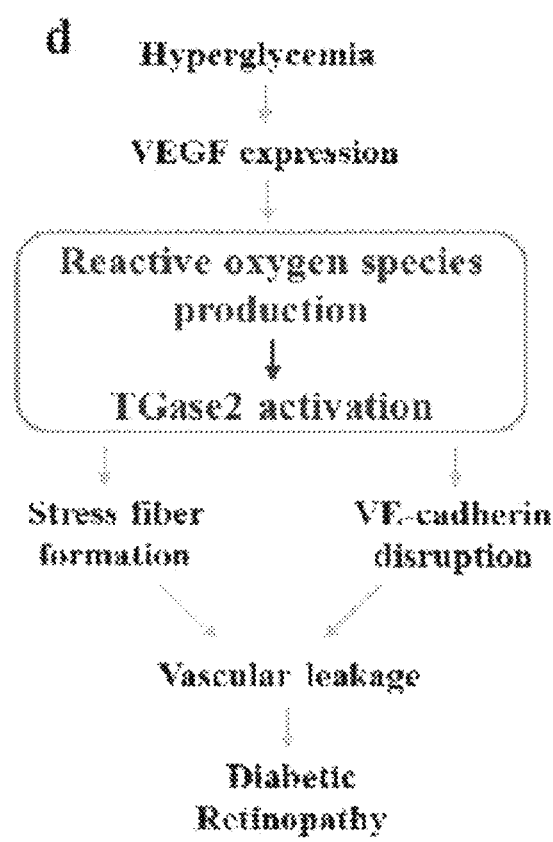
Figures 9A, 9B:
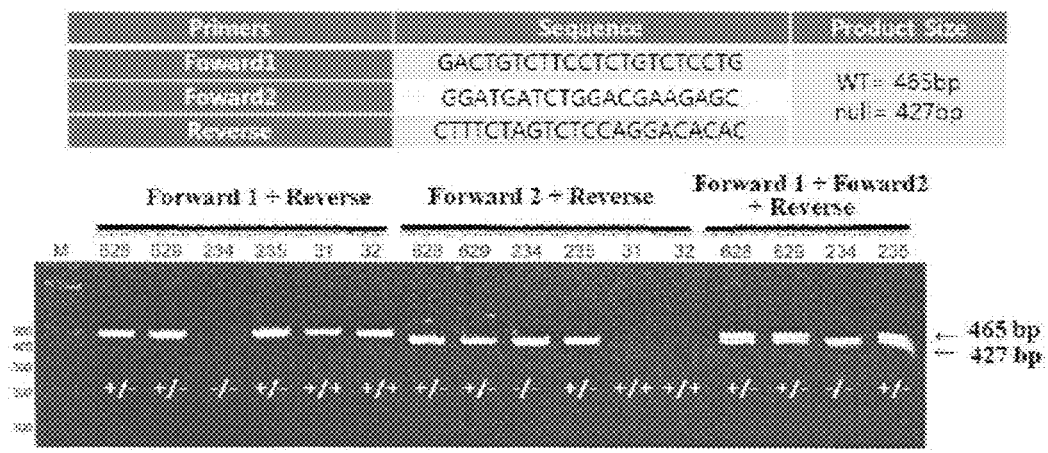
FIG. 9A shows the result of TGase2$^{-/-}$ mouse genotyping, in which DNA was extracted from the tail of a 3-week-old mouse and subjected to allele-specific PCR to determine the genotype, giving different bands between + and − alleles (forward 1 primer: wild type genotype (WT, 465 bp, +); forward 2 primer: deleted genotype (null, 427 bp, −))
FIG. 9B shows the physical parameters of TGase2$^{-/-}$ mouse.

Thus, since dopamine and cysteamine prevent vascular leakage by inhibiting TGase activity, preferably TGase2 activity and ROS generation, which is responsible for retinal vascular leakage in diabetic retinopathy, they may be useful for the treatment of diabetic complications associated with vascular leakage, such as diabetic retinopathy and nephropathy.

stress fiber formation and VE-cadherin disruption in the retinas of diabetic mice (FIG. 8D).

It is likely that TGase2 is a pivotal enzyme in the pathogenesis of diabetic complications. TGase2 is expressed in various ocular tissues including the cornea, retina, trabecular meshwork and lens, but the role of TGase 2 in diabetic retinopathy has not been known. In the present invention, the present inventors have elucidated the essential role of TGase2 in VEGF-induced vascular leakage in the retina of diabetic mice.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

```
                          SEQUENCE LISTING

<160> NUMBER OF SEQ ID NOS: 2

<210> SEQ ID NO 1
<211> LENGTH: 21
<212> TYPE: RNA
<213> ORGANISM: Homo sapiens

<400> SEQUENCE: 1
aagagcgaga ugaucuggaa c                                              21

<210> SEQ ID NO 2
<211> LENGTH: 31
<212> TYPE: PRT
<213> ORGANISM: Homo sapiens

<400> SEQUENCE: 2

Glu Ala Glu Asp Leu Gln Val Gly Gln Val Glu Leu Gly Gly Gly Pro
  1               5                  10                  15

Gly Ala Gly Ser Leu Gln Pro Leu Ala Leu Glu Gly Ser Leu Gln
                 20                  25                  30
```

In the present invention, the present inventors designed an in-vivo TGase activity assay using a confocal microscope and researched the critical role of TGase2 in VEGF-induced vascular leakage in the retina of diabetic mice. The present inventors demonstrated that hyperglycemia induces vascular leakage by activating TGase2 in the diabetic retina. VEGF activated TGase2 through the sequential elevation of intracellular $Ca^{2+}$ and ROS levels in endothelial cells. The TGase inhibitors cystamine and monodansylcadaverine (MDC) or TGase2-specific siRNA prevented VEGF-induced stress fiber formation and VE-cadherin disruption. The elevation of in-vivo TGase2 activity in the retinas of diabetic mice was inhibited by the intravitreal injection of TGase inhibitors. In addition, the intravitreal injection of TGase2 siRNA successfully inhibited hyperglycemia-induced TGase2 activation and microvascular leakage in the retinas of diabetic mice. C-peptide, which prevents VEGF-induced ROS generation and vascular leakage, inhibited in-vivo TGase2 activation in diabetic retinas. The ROS scavengers N-acetyl cysteine (NAC) and Trolox also inhibited hyperglycemia-induced activation of TGase2 in diabetic retinas. The role of TGase2 in VEGF-induced vascular leakage was further supported using diabetic TGase2$^{-/-}$ mice. Thus, our findings suggest that the ROS-mediated activation of TGase2 plays a key role in VEGF-induced vascular leakage by stimulating

What is claimed is:

1. A method for preventing or treating a diabetic retinopathy caused by vascular leakage comprising: administering to the subject a pharmaceutical composition comprising an effective amount of a TGase2 inhibitor,
   wherein the TGase inhibitor is any one selected from among monodansylcadaverine (MDC), dopamine, ethanolamine, a C-peptide and a TGase2-specific siRNA.

2. The method of claim 1, wherein the diabetic complication is caused by disruption of vascular integrity, which is induced by vascular endothelial growth factor (VEGF).

3. The method of claim 1, wherein the TGase2-specific siRNA has a sequence of SEQ ID NO. 1.

4. The method of claim 1, wherein the C-peptide has a sequence of SEQ ID NO. 2.

5. The method of claim 1, wherein the diabetic retinopathy caused by vascular leakage is induced by hyperglycemia.

6. The method of claim 1, wherein the TGase2 inhibitor inhibits vascular endothelial growth factor (VEGF)-induced TGase2 activation.

7. The method of claim 1, wherein the TGase2 inhibitor prevents vascular endothelial growth factor (VEGF)-induced disruption of vascular integrity and retinal microvascular leakage, which are caused by TGase2 activation.

8. The method of claim 1, wherein the TGase2 inhibitor has an antioxidant effect.

* * * * *